United States Patent
Sabuncu et al.

(10) Patent No.: US 12,032,048 B2
(45) Date of Patent: Jul. 9, 2024

(54) MACHINE LEARNING FOR SIMULTANEOUSLY OPTIMIZING AN UNDER-SAMPLING PATTERN AND A CORRESPONDING RECONSTRUCTION MODEL IN COMPRESSIVE SENSING

(71) Applicant: Cornell University, Ithaca, NY (US)

(72) Inventors: Mert R. Sabuncu, Ithaca, NY (US); Cagla D Bahadir, Ithaca, NY (US)

(73) Assignee: Cornell University, Ithaca, NY (US)

( * ) Notice: Subject to any disclaimer, the term of this patent is extended or adjusted under 35 U.S.C. 154(b) by 392 days.

(21) Appl. No.: 17/416,281

(22) PCT Filed: Dec. 20, 2019

(86) PCT No.: PCT/US2019/067887
§ 371 (c)(1),
(2) Date: Jun. 18, 2021

(87) PCT Pub. No.: WO2020/132463
PCT Pub. Date: Jun. 25, 2020

(65) Prior Publication Data
US 2022/0075017 A1     Mar. 10, 2022

Related U.S. Application Data

(60) Provisional application No. 62/783,892, filed on Dec. 21, 2018.

(51) Int. Cl.
*A61B 5/055*     (2006.01)
*A61B 5/00*      (2006.01)
(Continued)

(52) U.S. Cl.
CPC ............ *G01R 33/561* (2013.01); *A61B 5/055* (2013.01); *A61B 5/7203* (2013.01); *A61B 5/7267* (2013.01); *G01R 33/5608* (2013.01)

(58) Field of Classification Search
CPC .. G01R 33/561; G01R 33/5608; A61B 5/055; A61B 5/7203; A61B 5/7267;
(Continued)

(56) References Cited

U.S. PATENT DOCUMENTS 6,806,708 B1 * 10/2004 Lee .................... G01R 33/5611
                                                          324/309
2019/0369190 A1 * 12/2019 Ye ............................ G06N 3/08
(Continued)

OTHER PUBLICATIONS

International Search Report and Written Opinion dated Apr. 23, 2020 in International Application No. PCT/US2019/067887.
(Continued)

*Primary Examiner* — Ali Bayat
(74) *Attorney, Agent, or Firm* — McDermott Will & Emery LLP

(57) ABSTRACT

Systems and methods are disclosed for optimizing a sub-sampling pattern for efficient capture of a sub-sampled image to be reconstructed to form a high-resolution image, in a data-driven fashion. For example, Magnetic Resonance Imaging (MRI) scans can be accelerated by under-sampling in k-space (i.e., the Fourier domain). Since the reconstruction model's success depends on the sub-sampling pattern, optimization of the sub-sampling pattern can be combined with optimization of the model, for a given sparsity constraint, using an end-to-end learning operation. A machine-learning model may be trained using full-resolution training data that are under-sampled retrospectively, yielding a sub-sampling pattern and reconstruction model that are customized to the type of images represented in the training data. The disclosed Learning-based Optimization of the Under-sampling PattErn (LOUPE) operations may implement a convolutional neural network architecture, appended with a forward model that encodes the under-sampling process.

20 Claims, 11 Drawing Sheets

(51) Int. Cl.
*G01R 33/56* (2006.01)
*G01R 33/561* (2006.01)

(58) Field of Classification Search
CPC ............... A61B 5/4064; A61B 5/4585; A61B 2576/026; G06N 3/045; G06N 3/048; G06N 7/01; G06N 3/088
USPC ........................................................ 382/276
See application file for complete search history.

(56) References Cited

U.S. PATENT DOCUMENTS

| | | | |
|---|---|---|---|
| 2020/0034998 A1* | 1/2020 | Schlemper | G06F 17/18 |
| 2020/0058106 A1* | 2/2020 | Lazarus | G06V 10/764 |
| 2021/0224952 A1* | 7/2021 | Pawar | G06N 3/08 |

OTHER PUBLICATIONS

Aggarwal, Hemant Kumar, et al."Joint optimization of sampling patterns and deep priors for improved parallel MRI" arXiv preprint arXiv:1911.02945v1. Nov. 6, 2019.

Bahadir, Cagla D., et al. "Adaptive compressed sensing MRI with unsupervised learning" arXiv preprint arXiv:1907.11374v1. Jul. 26, 2019.

Gozcu, Baran, et al. "Learning-Based Compressive MRI", IEEE transactions on medical imaging. vol. 37, No. 6, pp. 1394-1406, May 2, 2018.

Schlemper, Jo, et al. "A Deep Cascade of Convolutional Neural Networks for Dynamic MR Image Reconstruction", rXiv preprint arXiv:1704.02422v2. Nov. 23, 2017.

Weiss, Tomer, et al., "Learning fast magnetic resonance imaging". arXiv preprint arXiv:1905.09324v1. May 22, 2019.

* cited by examiner

MACHINE LEARNING FOR SIMULTANEOUSLY OPTIMIZING AN UNDER-SAMPLING PATTERN AND A CORRESPONDING RECONSTRUCTION MODEL IN COMPRESSIVE SENSING

RELATED APPLICATIONS

The present application is a United States National Phase under 35 U.S.C. § 371 of International Application No. PCT/US2019/067887 filed on Dec. 20, 2019, which claims priority to, and the benefit of, U.S. Provisional Patent Application No. 62/783,892, titled "MACHINE LEARNING BASED OPTIMIZATION OF THE UNDER-SAMPLING PATTERN IN COMPRESSED SENSING IMAGING" and filed on Dec. 21, 2018, the entire contents of both of which are hereby incorporated by reference for all purposes.

TECHNICAL FIELD

The present subject matter relates generally to the field of compressive sensing, more specifically to medical imaging, with a demonstrated application in magnetic resonance imaging.

BACKGROUND

Compressive sensing is a technique that can be used to implement efficient imaging by collecting a smaller number of sensor measurements (under-sampling) than dictated by Shannon-Nyquist sampling theory. Compressive sensing is often used to accelerate Magnetic Resonance Imaging (MRI). However, it can be challenging to accurately produce a high quality image from under-sampled data.

MRI measurements are spatial frequency (Fourier) transform coefficients, also known as k-space data, and images are computed by solving the inverse Fourier transform that converts k-space data into the spatial domain. Medical images often exhibit considerable spatial regularity. For example, intensity values usually vary smoothly over space, except at a small number of boundary voxels. This regularity leads to redundancy in k-space and creates an opportunity for sampling below the Shannon-Nyquist rate (e.g., at a sampling frequency in k-space that is below the Shannon-Nyquist limit). Several Cartesian and non-Cartesian under-sampling patterns have been proposed in the literature and are widely used in practice, such as a Random Uniform pattern, a Variable Density pattern, and an equi-spaced Cartesian pattern with skipped lines.

A linear reconstruction of under-sampled k-space data (i.e., a direct inverse Fourier) yields aliasing artifacts, which are challenging to distinguish from real image features for regular sub-sampling patterns. Stochastic sub-sampling patterns, on the other hand, create noise-like artifacts that are relatively easier to remove. The classical reconstruction strategy in CS involves regularized regression, where a non-convex objective function that includes a data fidelity term and a regularization term is optimized for a given set of measurements. The regularization term reflects a priori knowledge of regularity in natural images. Common examples include sparsity-encouraging penalties such as L1-norm on wavelet coefficients and total variation.

In regularized regression, optimization is achieved via iterative numerical strategies, such as gradient-based methods, which can be computationally demanding. Furthermore, the choice of the regularizer is often arbitrary and not optimized in a data-driven fashion. Improved systems and methods for under-sampled imaging, including MRI imaging would therefore be desirable.

SUMMARY

The drawbacks described above can be addressed using machine learning approaches, which enable the use of models that learn from data and facilitate efficient and fast reconstructions.

There are two problems in compressive sensing: which samples to collect, and how to reconstruct a full-resolution image from the collected samples that are under-sampled? The former problem relates to the identification of the under-sampling pattern, while the latter problem can be referred to as the reconstruction problem. This application describes a novel computational framework to solve both of these problems simultaneously, using a data-driven machine-learning based approach. In the following discussion, the solution to these problems is sometimes described in connection with MRI images. However, the general principle can be used more broadly to optimize the sub-sampling pattern in any compressive sensing application.

The subject matter disclosed herein relates to a method of training a high-resolution image reconstruction system, while simultaneously optimizing the under-sampling mask for a desired sparsity level (also called under-sampling or acceleration rate).

The subject matter disclosed herein further relates to a method of training a MRI image reconstruction system. The method includes providing a set of input MRI images each having a corresponding image quality and a corresponding k-space; and processing the input MRI images using a neural network to collectively identify an under-sampling pattern and a reconstruction model for use in producing new MRI images, having an image quality that is substantially similar to the image quality of the input images, from under-sampled MRI data to be captured using the identified under-sampling pattern. The under-sampling pattern is configured to cause a k-space of the under-sampled MRI data to be under-sampled relative to the k-space of the input MRI images.

The subject matter disclosed herein further relates to a system for MRI imaging, the system includes a reconstruction system that includes a memory storing a plurality of reconstruction models and an indicator, for each reconstruction model, of an under-sampling pattern corresponding to that reconstruction model; and a processor. The processor is configured to receive under-sampled MRI data from an imaging system, where the under-sampled MRI data is under-sampled relative to a maximum sampling rate of the imaging system; receive, from the imaging system, an identifier of an under-sampling pattern with which the under-sampled MRI data was obtained by the imaging system; identify, using the identifier and the stored indicators, one of the stored reconstruction models corresponding to the under-sampling pattern with which the under-sampled MRI data was obtained by the imaging system; and process the under-sampled MRI data using the identified one of the stored reconstruction models to generate at least one MRI image, where the at least one MRI image has an improved image quality relative to an image quality of the under-sampled MRI data. The at least one MRI image may have an image quality that corresponds to an image quality of training data used to train a neural network to generate the plurality of reconstruction models and the corresponding under-sampling patterns. The under-sampled MRI data may have a corresponding k-space that is under-sampled relative to the k-space of the training data.

The subject matter disclosed herein further relates to a system that includes a training system configured to process a plurality of input images, each having a corresponding image quality and a corresponding sampling rate, using a neural network to collectively identify an under-sampling pattern and a reconstruction model; an imaging system configured to obtain under-sampled scan data that is under-sampled relative to the sampling rate of the input images, based on the under-sampling pattern; and a reconstruction system configured to generate output images having the image quality of the input images, from the under-sampled scan data obtained by the imaging system, using the reconstruction model.

The subject matter disclosed herein further relates to a system that includes a training system configured to process a plurality of high-resolution input images, each having a resolution, using a neural network to collectively identify an under-sampling pattern and a reconstruction model; an imaging system configured to obtain low-resolution image data based on the under-sampling pattern; and a reconstruction system configured to generate output images having a resolution that is substantially similar to the resolution of the high-resolution input images, from the low-resolution image data obtained by the imaging system, using the reconstruction model.

Experiments described herein with T1-weighted structural brain MRI scans show that the optimized sub-sampling pattern can yield significantly more accurate reconstructions compared to standard under-sampling schemes such as random uniform, variable density or equispaced under-sampling schemes.

BRIEF DESCRIPTION OF FIGURES

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

Dictionary learning techniques can be used to implement customized penalty terms in regularized regression-based reconstruction of under-sampled (e.g. MRI) images. For example, one strategy is to project the images (or patches) onto a "sparsifying" dictionary. Thus, a sparsity-inducing norm, such as L1, on the associated coefficients can be used as a regularizer. The drawback of such dictionary learning methods is that they still rely on iterative numerical optimization, which can be computationally expensive.

Recently, deep learning has been used to speed up and improve the quality of reconstruction of under-sampled MRI data. More specifically, models are trained on data to learn to map under-sampled k-space measurements to image domain reconstructions. For a new data point, this computation is often non-iterative and achieved via a single forward pass through an "anti-aliasing" neural network, which is computationally efficient. However, these machine learning-based methods are typically optimized for a specific under-sampling pattern that is static and is provided by the user. Under-sampling patterns can also be optimized for given a reconstruction method. The reconstruction model's performance will depend significantly on the sub-sampling pattern.

In the present disclosure, systems and method are provided for optimizing the sub-sampling pattern in a data-driven fashion. The disclosed systems and methods optimize the sub-sampling pattern and reconstruction model collectively (e.g., substantially simultaneously), using an end-to-end learning strategy. This collective determination of the sub-sampling pattern and the reconstruction model is made possible by two properties of deep learning-based reconstruction models: their speed and differentiable nature. These properties enable the rapid evaluation of the effect of small changes to the sub-sampling pattern on reconstruction quality.

Figure 1:
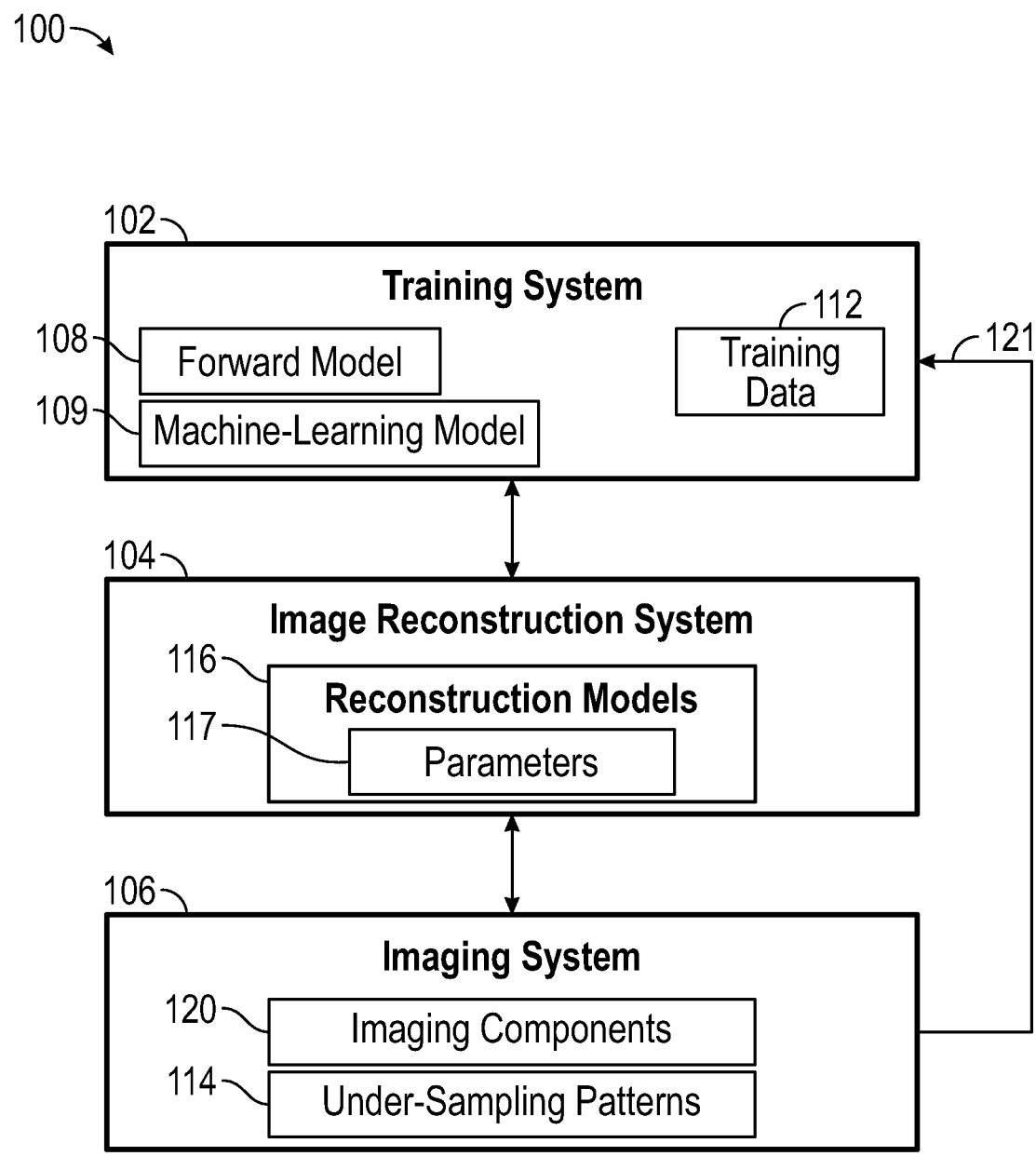
FIG. 1 illustrates a schematic view of a system, according to aspects of the disclosure.

FIG. 1 illustrates a block diagram of a system that implements various aspects of the subject technology. In the example of FIG. 1, a system 100 includes a training system 102, an image reconstruction system 104, and an imaging system 106. In one illustrative example, the training system 102 may process a plurality of input MRI images, each having a corresponding image quality and a corresponding k-space, using a neural network to collectively identify an under-sampling pattern 114 and a reconstruction model 116. The input images may be fully sampled images, meaning that the images were obtained with the highest sampling capability of the imaging system with which they were obtained. The input images may be referred to a ground truth images herein since, for the purposes of training, the input images represent the most truthful available representation of the object being imaged. Whether or not the input images are fully sampled, the input images may be high-resolution images, having a resolution that is higher than scan data to be obtained by imaging system 106 based on under-sampling patterns 114. During training operations, training system 102 may reduce the resolution of the high-resolution images (e.g., based on an under-sampling pattern) to generate under-sampled data with which to train machine-learning model 109 and optimize the under-sampling patterns.

The corresponding k-space of each input MRI image may be a Fourier transform of that input MRI image. The number of data points in the k-space may represent a sampling rate or sampling frequency of a particular image. The image quality of each input image may be a quantitative measure of image quality corresponding one or a combination (e.g., a weighted combination) of a signal-to-noise ratio of the image, a peak signal-to-noise ratio (PSNR), a resolution of the image such as determined by the maximum extent of the k-space covered, a contrast of the image, an amount of aliasing in the image, a sharpness of the image, a dynamic range of the image, an amount of distortion in the image, an amount of vignetting in the image, a number of artifacts in the image, or the like.

The imaging system 106 may obtain under-sampled scan data based on the under-sampling pattern, and the reconstruction system 104 may generate output images having approximately the image quality and/or the resolution of the (e.g., high-resolution) input images, from the under-sampled scan data obtained by the imaging system, using the reconstruction model 116. In this way, the system 100 can generate high-resolution and/or high-quality images, based on under-sampled (e.g., low resolution) scans of a subject, using a reconstruction model that has been optimized for the under-sampling pattern used to collect the scans. The output image may be determined to have approximately the image quality of the input image when, for example, the quantitative image quality of the output image is within a predetermined range of the image quality of the output image. The predetermined range may be a fixed or variable range and may be an absolute range (e.g., a range of signal-to-noise ratios) or a statistical range (e.g., within one, two, three or more sigma of the signal-to-noise ratio of the input image). The output image may be generated with a resolution that is substantially the same as the resolution of the input images used by training system 102 for training the reconstruction models, even when the under-sampled scan data has a lower resolution than the resolution of the input images.

Imaging system 106 may be a magnetic resonance imaging (MRI) system that includes imaging components 120 such as one or more emission inducing components (e.g., one or more superconducting magnets and/or other magnetic components that induce the patient's tissue to emit electromagnetic radiation) and/or one or more receiving components that capture the emission from the patient's tissues as MRI data. However, it should also be appreciated that imaging system 106 may be implemented as another type of medical imaging system such as a computerized tomography (CT) scanning system, or any other type of compressed imaging system that reconstructs high-resolution images from relatively lower resolution images, such as under-sampled images.

Imaging system 106 may capture under-sampled image data (e.g., sampled at less than the Shannon-Nyquist rate in image space and/or in k-space) according to one or more under-sampling patterns 114. The under-sampling patterns 114 may be stored at imaging system 106, or may be retrieved from a remote location such as from the image reconstruction system 104 or the training system 102. The under-sampling patterns 114 may, for example, be implemented as mask images in image space and/or in k-space (i.e., the Fourier domain) that indicate, to imaging system 106, locations in image space and/or in k-space at which to capture data with imaging components 120, and where not to capture data.

The under-sampling patterns 114 may be generated by the training system 102 (as described in further detail hereinafter) and provided to the imaging system 106 and/or the image-reconstruction system 104. The under-sampling patterns 114 may include an under-sampling pattern for each of several parts of a human or animal body and/or for each of several scan sequences (e.g. T2-weighted, T1-weighted, Proton Density, DWI etc.) and/or for each part of the body. For example, under-sampling patterns 114 may include under-sampling patterns that are specific to a particular organ such as a human heart, a human liver, a human pancreas, a human brain, etc., specific to a particular non-organ part of the body such as a human knee, a human elbow, a human foot, a human shoulder, etc., specific to a part or organ of a body of a non-human animal, or specific to any other object for which reconstruction of high-resolution images from under-sampled image data, such as low-resolution images, is desired. The under-sampling patterns 114 may also include under-sampling patterns that are specific to a particular scan sequence for a particular body part or organ such as an under-sampling pattern 114 for a lesion detection scan of a human brain or an under-sampling pattern 114 for a hemorrhage detection scan of a human brain.

The imaging system 106 may provide captured under-sampled data, such as MRI data, that has been captured using imaging components 120 based on a particular under-sampling pattern 114, to the image reconstruction system 104. An indicator of the under-sampling pattern 114 that was used to obtain that under-sampled data may also be provided from the imaging system 106 to the reconstruction system.

In order to reconstruct a high-resolution and/or high image quality image from the under-sampled (e.g., low-resolution) data provided by the imaging system 106, image reconstruction system 104 obtains a reconstruction model 116 corresponding to the indicated sub-sampling pattern 114. The image reconstruction system 104 may store a database of reconstruction models 116 (e.g., each corresponding to an optimization of machine-learning model 109, and including parameters 117 such as weights that have been optimized for a corresponding sub-sampling pattern 114 by training system 102). Each reconstruction model 116 may be stored in connection with an indicator of a corresponding under-sampling pattern 114. When the under-sampled data and the indicator of the under-sampling pattern 114 that was used to obtain that under-sampled data are received at the image reconstruction system 104, the image reconstruction system may then obtain the appropriate reconstruction model 116 using the received indicator.

Image reconstruction system 104 can then reconstruct a high-resolution and/or high-quality image from the relatively lower resolution (under-sampled) data obtained by imaging system 106, by applying the obtained reconstruction model 116 to that data. The reconstructed image may be provided for display at a display of the imaging system or for transmission or storage. For example, the reconstructed image may be displayed at a display of the imaging system 106 in real time during an imaging scan (e.g., to be viewed by a technician of a medical practitioner while additional data are being collected).

Image reconstruction system 104, training system 102, and/or imaging system 106 may be collocated (e.g., in a common area of a hospital for medical imaging), or one or more of image reconstruction system 104, training system 102, and/or imaging system 106 may be located remotely from one or more others of image reconstruction system 104, training system 102, and/or imaging system 106 and communicatively coupled to the one or more others of image reconstruction system 104, training system 102, and/or imaging system 106 by a network (e.g., a local area network and/or a wide area network such as the Internet).

Training system 102 operates to generate the under-sampling patterns 114 and the reconstruction models 116 that correspond to (e.g., that are optimized for use with) each under-sampling pattern. As shown in FIG. 1, the training system 102 may implement a forward model 108 that encodes the under-sampling process and a machine-learning model 109. Training system 102 trains the machine-learning model 109 (e.g., by adjusting parameters of the model) with training data 112 to generate the reconstruction models 116 corresponding to each under-sampling pattern 114. For example, training system 102 may include one or more processors for running a deep neural network (DNN) algorithm corresponding to the machine-learning model 109. The one or more processors may be local, forming a server or a cluster, or distributed in the cloud. In an implementation, the DNN includes a convolutional neural network (CNN) such as a fully convolutional CNN. For example, in an implementation, the DNN is based on the "U-Net" convolutional neural network that was developed for biomedical image segmentation at the Computer Science Department of the University of Freiburg, Germany.

Since the performance of a reconstruction model 116 in generating reconstructed images based on under-sampled data depends on the sub-sampling pattern with which the under-sampled data is obtained, training system 102 combines the process of identifying an under-sampling pattern with the process of training a reconstruction model in a single learning operation. For example, for a given sparsity constraint (which may be user-provided or may also be learned by training system 102), training system 102 may optimize the under-sampling pattern 114 and reconstruction model 116 for a particular scan sequence, using an end-to-end learning operation. The end-to-end learning operation may be performed by modifying the convolutional neural network architecture (e.g., the U-Net) appended with the forward model 108 that encodes the under-sampling process. Training system 102 may thus provide reconstruction models and corresponding under-sampling patterns in model/pattern pairs from a single end-to-end training system based on the neural network.

Training data 112 may include full-resolution images such as full-resolution MRI images, captured during previous MRI scans of various subjects (e.g., at the full (maximum) resolution of an MRI imaging system). In some cases, training data 112 may include images that are not fully-sampled or full-resolution. Training data 112 can also include CT images or sinograms or other type of medical imaging data, or natural images (e.g., landscapes, portraits, animal images etc.) depending on the application. In general, for purposes of the present discussion, training data 112 may be referred to as ground truth images, whether the images are full-resolution image, high-resolution but less than full resolution images, MRI images or other input images to the training system.

During training operations to identify under-sampling patterns 114 and corresponding reconstruction models 116, the training data 112 (e.g., ground truth images) is provided to the forward model 108. The forward model converts the ground truth images to k-space and then down-samples the k-space according to a particular learned under-sampling pattern. The model then converts the down-sampled k-space (now under-sampled relative to the k-space of the input image) to the image domain to generate under-sampled images corresponding to a ground truth image and the particular under-sampling pattern, to feed as an input to the reconstruction network. It should be appreciated that the down-sampling operation sometimes lowers the resolution of the input image, but sometimes does not, depending on the under-sampling pattern. For example, in cases in which the highest k-space coverage of the under-sampling pattern is same as the highest k-space coverage corresponding to the ground truth image, the under-sampled image has the same resolution as the ground truth image, though it is relatively under-sampled and thus likely has a reduced image quality. Accordingly, the terms "high-resolution" and "low-resolution" are sometimes used herein to reflect the loss of high-frequency content in the k-space caused by down-sampling input images data.

The forward model can also operate in the k-space and skip the k-space-to-image conversion, if, for example, the reconstruction model is arranged to operate with k-space as input. The machine-learning model 109 then reconstructs an output (e.g., high-resolution such as full-resolution) image from the input under-sampled (e.g., low-resolution) image, which is then compared (e.g., in image quality) to the original ground truth image to determine the quality of the reconstruction. By adjusting the under-sampling pattern and the parameters (e.g., weights) of the reconstruction model in an end-to-end operation, pairs of patterns and reconstruction models can be generated for each set of input ground truth images. Each set of ground truth (e.g. fully-sampled, full-resolution or other input images depending on the limitations of the applications) training images may be images obtained during a particular (e.g. ground truth, fully-sampled, or sampled to the best ability depending on the limitations of the applications) scan sequence for a particular body part or organ. The network can also be trained on already under-sampled images in some cases (e.g., if the imaging system is not able to acquire fully-sampled images or if it is not preferred). In such cases, the model learns by further under-sampling the already under-sampled training images. The fully-sampled (or sampled to the highest capacity of the imaging system) ground truth input images generally have higher resolution, detail, and image quality compared to the under-sampled (e.g., low-resolution) images generated by down-sampling the k-space of those images. The output reconstructed images, generated from the down-sampled k-space using the reconstruction model(s) may be high-quality and/or high-resolution images that have approximately the same level of detail and quality as the ground truth images.

Once an under-sampling pattern/reconstruction model pair has been generated by the training system 102, the under-sampling pattern 114 may be provided to imaging system 106 and the reconstruction model 116 for that under-sampling pattern 114 may be provided to reconstruction system 104. In this way, when imaging system 106 performs a fast and efficient under-sampled scan using the under-sampling pattern 114, reconstruction system 104 can use the reconstruction model 116 that has been generated specifically for that under-sampling pattern to reconstruct an output image (e.g., with the image quality of the input training images) from the data from the under-sampled scan. The under-sampling pattern can also be used with other reconstruction techniques if the specifically trained reconstruct model is not available in the imaging or reconstruction system.

In this way, the machine-learning model learns from ground truth data that are under-sampled retrospectively, yielding a sub-sampling pattern and reconstruction model that are customized to the type of images represented in the training data. The operations for cooperatively determining an under-sampling pattern and a corresponding reconstruction model are sometimes referred to herein as LOUPE (Learning-based Optimization of the Under-sampling PattErn) operations. As described in further detail hereinafter, experiments with T1-weighted structural brain MRI scans show that the sub-sampling patterns 114 described herein can yield significantly more accurate reconstructions compared to standard random uniform, variable density, or equispaced under-sampling schemes.

It should also be appreciated that, as indicated by feedback arrow 121, in some operational scenarios, scan data for a particular subject may be provided to training system 102 (e.g., in real time during a scanning session for the subject). This scan data for the subject can be incorporated in the training data 112 so that the under-sampling pattern 114 and the corresponding reconstruction model 116 are specific to the subject being scanned. For example, the imaging system 106 may obtain one or more initial scans of a subject and provide initial scan data for the subject to the training system 102. The training system 102 can then generate the under-sampling pattern and the reconstruction model in real time based on the input training images and the initial scan data for the subject, to be used to perform subsequent under-sampled scans and reconstructions for the same subject.

Figure 2:
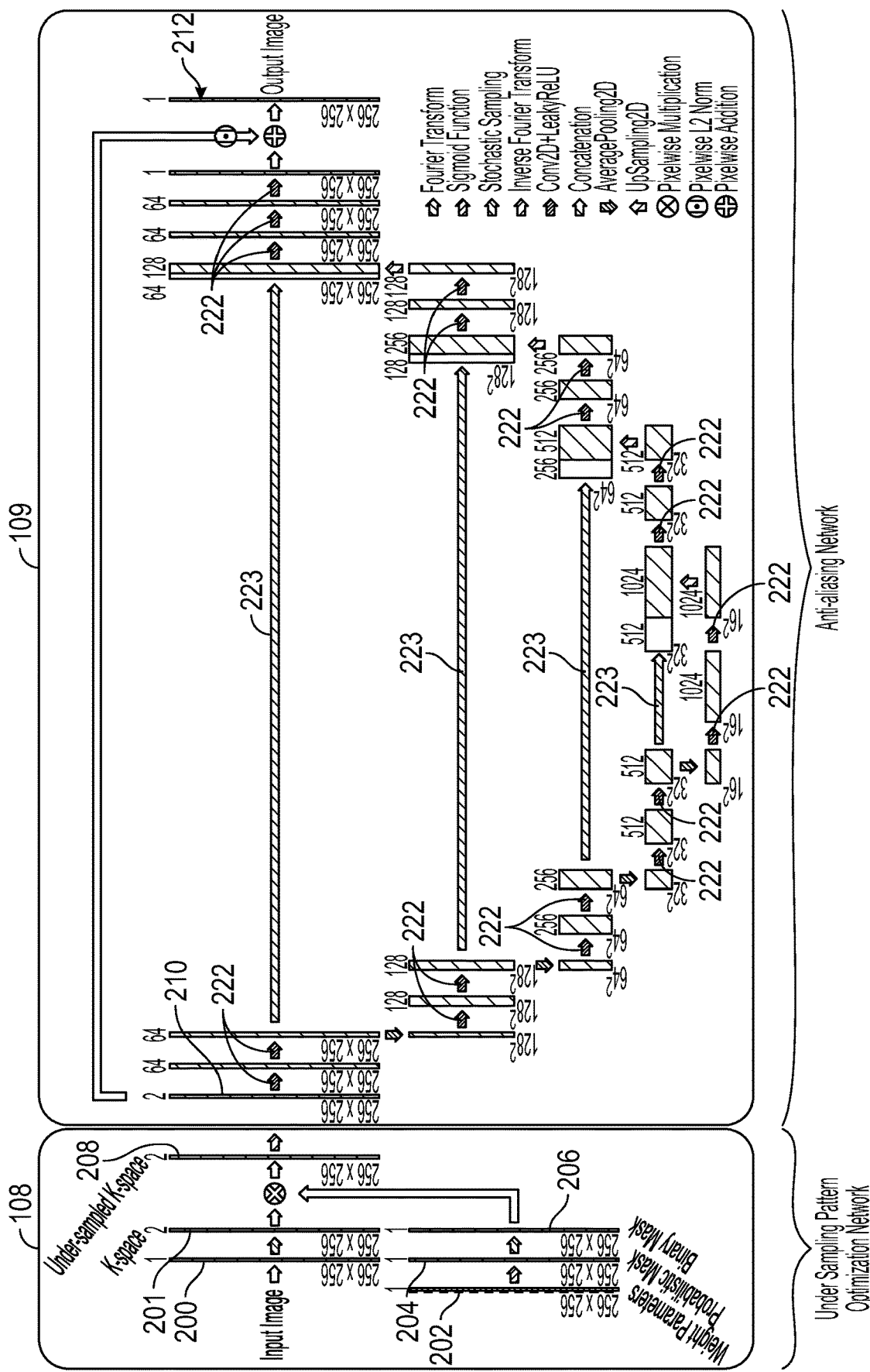
FIG. 2 represents a flow diagram illustrating operations in an end-to-end joint learning operation for determination of an under-sampling mask and a corresponding reconstruction model for reconstructing under-sampled images, according to aspects of the disclosure.

FIG. 2 illustrates a diagram of operations that may be performed for (e.g., simultaneously) determining a sub-sampling pattern 114 and a set of model parameters 117 for a corresponding reconstruction model 116, such as for a particular organ, body part, or scan sequence.

In the example of FIG. 2, the neural network architecture for LOUPE are illustrated with vertical solid lines, each representing a 2D image, with the number of channels indicated above the line and the size of the image shown on the lower left side of the line. This architecture can also be extended to be used for 3D volumes and incorporate multi-channel inputs (e.g. Multi-channel imaging in MRI etc.) The under-sampling operation can be conducted in three dimensions or can be limited to one or two dimensions in the training, depending on the application.

As indicated in FIG. 2, an input image 200 is provided to forward model 108 (e.g., the under-sampling pattern optimization network). The input image 200 is a full- or high-resolution image (also can be full-sampled, or sampled to the best ability of the scanning parameters), sometimes described herein as a ground truth image. In the example of FIG. 2, the input image 200 is Fourier transformed to k-space, and then downsampled by pixel-wise multiplication with a particular under-sampling (binary, or close to binary) mask 206. The vertical dashed line in FIG. 2 represents a 2D real-valued image 202 of weight parameters 117, where one parameter is learned at each location, which is then passed through a sigmoid to yield the probability mask 204 (denoted asp in the following discussion).

Previous attempts at optimizing a sub-sampling pattern for MRI scans, without optimizing a corresponding reconstruction model, include the OEDIPUS framework, which uses the information-theoretic Cramer-Rao bound to compute a deterministic sampling pattern that is tailored to the specific imaging context, and using a Bayesian approach to optimize k-space sampling trajectories under sparsity constraints. Using a Bayesian approach is computationally expensive and does not scale well to large datasets. To alleviate this drawback, a computationally more efficient strategy can be applied to optimize the under-sampling trajectory. However, these approaches do not consider a sophisticated reconstruction technique and, instead, merely optimize for the simple method of inverse Fourier transform with zero-filling.

In accordance with aspects of the subject disclosure, LOUPE operations are described in which the optimized probabilistic sub-sampling mask is generated together with a rapid neural network-based reconstruction model. For example, as illustrated in FIG. 2, the LOUPE operations are trained using an end-to-end unsupervised learning approach with retrospectively sub-sampled images.

The LOUPE systems and methods illustrated in FIG. 2 consider the two fundamental problems of compressed sensing simultaneously: the optimization of the under-sampling pattern 114 and learning a reconstruction model 116 that rapidly solves the ill-posed anti-aliasing problem.

The LOUPE operations illustrated in FIG. 2 determine a "probabilistic mask" 204 (denoted asp in the following discussion) that describes an independent Bernoulli (binary) random variable B at each k-space (discrete Fourier domain) location on a full-resolution or high-resolution (e.g., higher resolution than the resolution of the under-sampled data to be obtained, or ground truth) grid. Thus, a probabilistic mask p is an image 204 of probability values in k-space. A binary under-sampling mask 206 (denoted as m in the following discussion) has a value of 1 (0) that indicates that a sample is (not) acquired at the corresponding k-space point. In order to train the machine-learning model with a binary mask 206, in some implementations, a straight-through estimator may be used. We assume m is a realization of $M \sim \Pi_i \mathcal{B}(p_i)$, where i is the k-space location index. Binary mask 206 may store the under-sampling pattern 114 corresponding to each learned reconstruction model 116. Let $x_j$ denote a full-resolution (e.g., 2D) MRI slice 200 in the image (spatial) domain, where j is the scan index. While p, M, m and $x_j$ are defined on a 2D grid (in k-space or image domain), they are vectorized in the following mathematical expressions. Thus the systems and methods described herein are not constrained to 2D images and can be applied 3D sampling grids as well.

The LOUPE operations described herein solve, for example, the following optimization problem:

$$\underset{p,A}{\operatorname{argmin}} \, \mathbb{E}_{M \sim \Pi_i \mathcal{B}(p_i)} \left[ \lambda \sum_i M_i + \sum_i \left\| A\!\left(f^H \operatorname{diag}(M) F x_j\right) - x_j \right\|_1 \right], \quad (1)$$

where F is the (forward) Fourier transform matrix, $F^H$ is its inverse (i.e., the Hermitian transpose of F), A(•) is an anti-aliasing (de-noising) function that is parameterized via a neural network, $M_i \sim \mathcal{B}(p_i)$ is an independent Bernoulli, diag(M) is a diagonal matrix with diagonal elements set to M, $\lambda \in \mathbb{R}^+$ is a hyper-parameter, and $\|\cdot\|_1$ denotes the L1-norm of a vector. The L1-norm can also be switched to L2-norm, or other metrics such as SSIM, PSNR etc. depending on training purposes. In accordance with aspects of the subject disclosure, $x_j$ is real-valued, F and $F^H$ are complex valued, and A(•) accepts a complex-valued input. The output of A is a real-valued output image 212. Furthermore, $x_j$ and the output of A can also be complex valued.

The first term in Eq. (1) above is a sparsity penalty that encourages under-sampling by encouraging the number of k-space points that will be sampled to be small. The hyper-parameter $\lambda$ controls the influence of the sparsity penalty, where higher values yield a more aggressive sub-sampling factor. The second term in Eq. (1) above can be approximated using a Monte Carlo approach. Thus the example LOUPE optimization problem becomes $$\underset{p,A}{\operatorname{argmin}} \, \lambda \sum_i p_i + \sum_j \frac{1}{K} \sum_{k=1}^{K} \left\| A\!\left(F^H \operatorname{diag}(m^{(k)}) F x_j\right) - x_j \right\|_1, \quad (2)$$

where $m^{(k)}$ is an independent binary mask realization of $M \sim \Pi_i \mathcal{B}(p_i)$, and in an operation with K samples. The second term of Eq. (2) above and be further re-parameterized as shown in Eq. (3):

$$\underset{p,A}{\operatorname{argmin}} \, \lambda \sum_i p_i + \sum_j \frac{1}{K} \sum_{k=1}^{K} \left\| A\!\left(F^H \operatorname{diag}(u^{(k)} \le p) F x_j\right) - x_j \right\|_1, \quad (3)$$

where $u^{(k)}$ is a realization of a random vector of independent uniform random variables on [0, 1], and $u^{(k)} \le p$ is a binary random vector where each entry is set to 1 if the inequality is satisfied, and 0 otherwise.

It should be appreciated that the optimization problem described in connection with Equations (1)-(3) above and Equation (4) below is representative and can vary. The mathematical description herein is one example instantiation, which can be modified without deviating from the spirit of the invention.

In an implementation, the LOUPE systems and methods described herein are implemented using deep neural networks, which solve the learning problem via stochastic gradient descent. To make the loss function differentiable everywhere (continuously differentiable), the thresholding operation in Eq. (3) can be relaxed via a sigmoid, as shown in Eq. (4):

$$\underset{p,\theta}{\operatorname{argmin}} \, \lambda \sum_i p_i + \sum_j \frac{1}{K} \sum_{k=1}^{K} \left\| A_\theta\!\left(F^H \operatorname{diag}(\sigma_s(u^{(k)} - p)) F x_j\right) - x_j \right\|_1, \quad (4)$$

where $$\sigma_s(a) = \frac{1}{1 + e^{-sa}}$$

is a sigmoid with a slope s, and $A_\theta$ denotes a neural network parameterized with weights 202 (denoted as $\theta$ in the present discussion). The slope for this sigmoid can be set to be sufficiently steep to approximate the thresholding step function.

The anti-aliasing function $A_\theta$ can be implemented as a convolutional neural network such as a fully-convolutional neural network. In one example, $A_\theta$ builds on the widely used U-Net architecture.

As indicated in FIG. 2, the forward model 108 applies a forward discrete Fourier transform, F, converting an input image 200 into k-space. The k-space measurements 201 are next under-sampled by a binary mask 206 (denoted as m in the equations above), which is a Monte Carlo realization of the probabilistic mask 204 (denoted asp). The values of the probabilistic mask 204 are treated as unknown parameters that are learned during the training process depicted in FIG. 2. As shown, the binary mask 206 is multiplied element-wise with the k-space data 201 (equivalent to retrospective under-sampling by inserting zeros at missing points), to form an under-sampled image 208, which is then passed to an inverse discrete Fourier transform FH to form image 210.

This image 210, which will typically contain aliasing artifacts, is then provided as input to the anti-aliasing network Ae, as shown in FIG. 2. This network takes a complex-valued under-sampled image, represented as two-channels, and aims to minimize the reconstruction error— the squared difference between the magnitude images of ground truth and the reconstruction.

Thus, the input to Ae is a two-channel 2D under-sampled image 210 from forward model 108, the channels of which correspond to the real and imaginary components. The U-Net estimates the difference between the reconstruction 212 (i.e., the result of applying the inverse Fourier transform to the zero-filled under-sampled k-space measurements), and the ground truth image 200. Finally, the probabilistic mask 204 (denoted asp in the equations above) is formed by passing an unrestricted real-valued image 202 through a sigmoid.

FIG. 2 illustrates the full architecture that combines all of these elements. The arrows 222 represent 2D convolution layers with a kernel size 3×3, and a Leaky rectified linear unit (ReLU) activation followed by Batch Normalization. The convolutions may use zero-padding to match the input and output sizes. The activation function can also be chosen as tanh, or other suitable functions. The kernel size, padding options (e.g. zero, constant, replicate), usage of Batch Normalization are dependent on the implementation. The arrows 223 indicate skip connections, which correspond to concatenation operations. Machine-learning model 109 may also implement a stochastic sampling layer that draws uniform random vectors u). This is similar to the Monte Carlo strategy used in variational neural networks.

The reconstruction models 116 resulting from the training of the anti-aliasing network (e.g., machine-learning model 109) are trained on a collection of input images 200 such as ground truth, high-resolution, and/or full-resolution images (corresponding to a collection of $\{x_j\}$ in the notation above). Images 200 can be provided from an external system as images, or can be generated from raw scan data (e.g., MRI data) received from imaging system 106 or from an external system, in some scenarios. Thus, training system 102 can perform the LOUPE operations illustrated in FIG. 2, to minimize the unsupervised loss function of Eq. (4) using an end-to-end learning strategy to obtain the probabilistic mask p and the weights θ of the anti-aliasing network Ae. The hyper-parameter A can be set empirically to obtain the desired sparsity, or can be determined as part of the LOUPE operations. For example, the machine-learning model 109 can, in some implementations, include a renormalization layer that helps ensure that the mask sparsity is the final sparsity.

The neural network can be implemented, for example, in the Keras open-source neural-network library written in Python, with, for example, the Tensor-Flow open source library as the back-end and using layers from the publicly available Neuron library. In an implementation, the publicly available ADAM optimizer based on an adaptive learning rate method, can be used with, for example, an initial learning rate of 0.001 and terminate learning when validation loss plateaus. In an implementation, a mini-batch size of 32, and K=1 can be used. The input images 200 can be randomly shuffled. The network can also be implemented with different settings, for example, in Pytorch with different optimizer, learning rate, batch size and K values.

As illustrated in the example of FIG. 2, training system 102 may down-sample input (e.g., ground truth, high-resolution, and/or full resolution) images 200 according to a test under-sampling pattern corresponding to binary mask 206, to form under-sampled images 208 each having a corresponding k-space that is under-sampled relative to the k-space of the input (e.g., ground truth) images 200. As discussed herein, down-sampling the input images may reduce the resolution of high-resolution input images to form relatively low-resolution images having a resolution that is lower than the resolution of the high-resolution input images. Training system may also generate, using the neural network implemented as an anti-aliasing network 109, output reconstructed images 212 (e.g., having the resolution of the high-resolution images 200) from the under-sampled (e.g., low resolution) images. The training system 102 may then minimize the unsupervised loss function (e.g., the function defined in Eq. (4)) that is based on a difference between the ground-truth images 200 and the output reconstructed images 212, by adjusting weights 202 of the anti-aliasing network and adjusting the test under-sampling pattern corresponding to binary mask 206.

Thus, as illustrated in FIG. 2, the entire pipeline for determining an under-sampling mask and a corresponding reconstruction model can be made up of two building blocks in a single end-to-end system: the first optimizing the under-sampling pattern, and the second solving the reconstruction problem.

Empirical Analysis

The following discussion describes an empirical analysis including results obtained by operating a training system as described in FIG. 1 to perform a LOUPE operation as illustrated in FIG. 2. In this empirical analysis, 3D T1-weighted brain MRI scans from the multi-site ABIDE-1 study were used as training and test data. In particular, one hundred high quality volumes, as rated by independent experts via visual assessment, were used for training the disclosed LOUPE models, while a non-overlapping set of fifty subjects were used for validation. For testing the LOUPE operations and other operations for comparison, ten held-out independent test subjects were used. All experiments were conducted on 2D axial slices, which consisted of 1×1 mm2 pixels and were of size 256×256. One hundred seventy-five slices were extracted from each 3D volume, which provided full coverage of the brain, the central region of interest in this portion of the empirical analysis, and excluded slices that were mostly background.

During testing, a peak signal to noise ratio (PSNR) between reconstructions 212 generated using various different reconstruction models and the ground truth images 200 for each volume were computed. PSNR is a standard metric of reconstruction quality (e.g., image quality) used in compressed sensing MRI. Quantitative results with other metrics (though not included herein) were also consistent.

For comparison with the disclosed reconstruction models that were optimized together with the under-sampling patterns, reconstructions were also performed using several benchmark models and several conventional under-sampling patterns. The first benchmark method is the Annihilating Filter-based Low-Rank Hankel Matrix (ALOHA) method, which uses a low-rank Hankel matrix to impute missing k-space values. Reconstructions performed using ALOHA employed the code distributed by the authors thereof. Since the default setting did not produce acceptable results on our data, the input parameters for ALOHA were optimized to minimize the mean absolute error on a training subject.

The second benchmark reconstruction method is a regularized regression technique that combines total generalized variation (TGV) and the shearlet transform. This method has been demonstrated to yield excellent accuracy in compressed sensing MRI. Reconstructions performed using TGV used the code provided by the authors thereof.

The third benchmark method is based on the Block Matching 3D (BM3D) method, which was recently shown to offer high quality reconstructions for under-sampled MRI data. BM3D is an iterative method that alternates between a de-noising step and a reconstruction step. Reconstructions performed using BM3D employed the open source code therefor.

The fourth benchmark method is a U-Net-based reconstruction method, similar to the recently proposed deep residual learning for anti-aliasing technique of Le et al. "Deep residual learning for compressed sensing MRr" in Biomedical Imaging (ISBI) 2017. This reconstruction model is similar to the U-Net reconstruction model used in the disclosed LOUPE systems and methods, with an important difference: in the benchmark implementation, the anti-aliasing model is trained from scratch, for each sub-sampling mask, separately. In the disclosed LOUPE systems and methods, a U-Net model is trained jointly with the optimization of the sub-sampling mask.

In the empirical analysis, for comparison with the reconstructions using the under-sampling patterns 114 jointly determined with the corresponding reconstruction models 116, reconstructions were also performed using three different conventional sub-sampling patterns that are widely used in the literature: a Random Uniform sub-sampling pattern, a Random Variable Density sub-sampling pattern, and an equispaced Cartesian sub-sampling pattern. All of the conventional sub-sampling patterns include a fixed 32×32 "calibration region" in the center of the k-space. The calibration region is a fully sampled rectangular region around the origin, and has been demonstrated to yield better reconstruction performance when using conventional sub-sampling patterns. In the empirical analysis, experimental reconstructions were performed excluding the calibration region and sub-sampling over the entire k-space. However, reconstruction performance was no better than including the calibration region, so we omit these results from this discussion.

Figure 3:
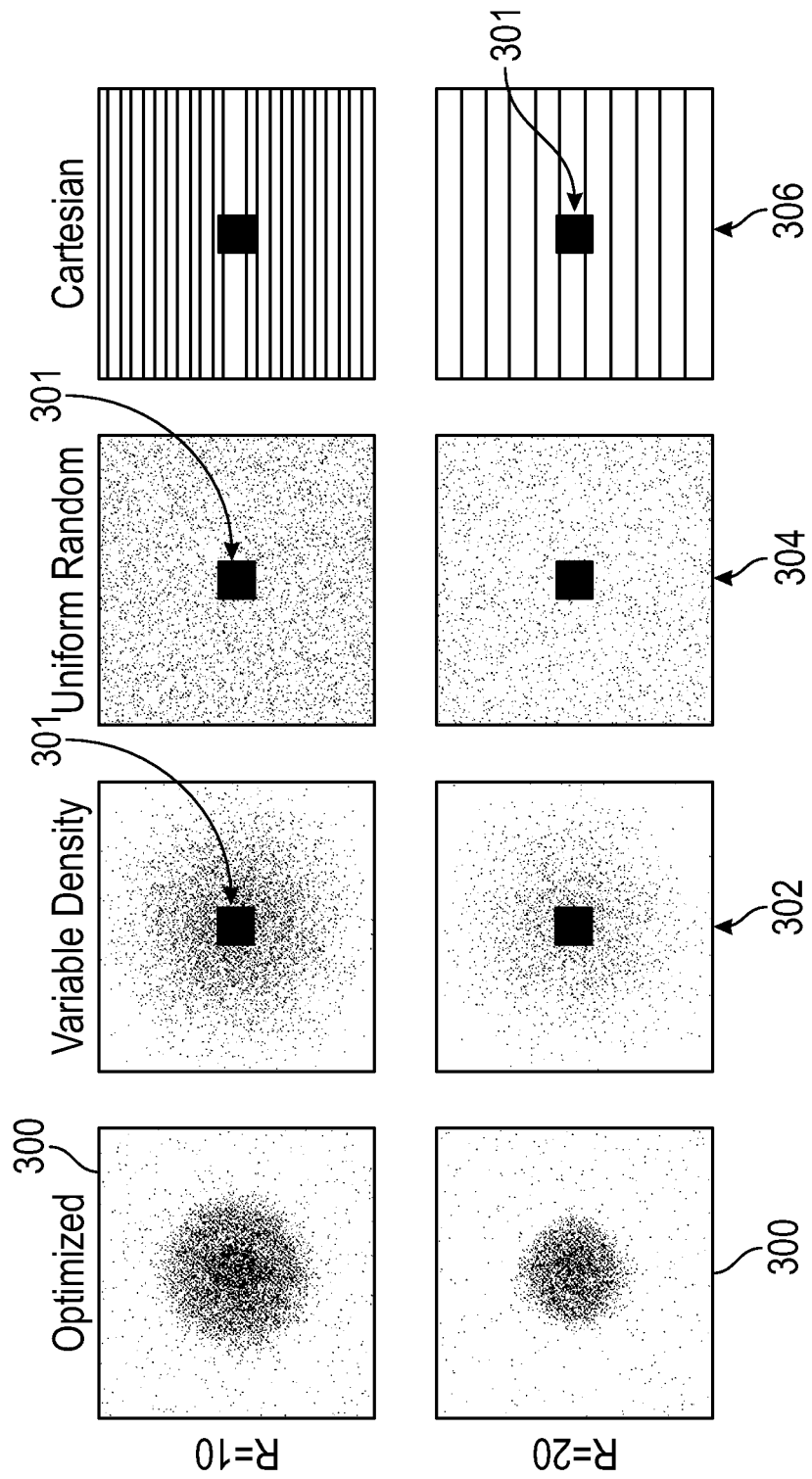
FIG. 3 illustrates various sub-sampling masks, according to aspects of the disclosure.

FIG. 3 shows examples of optimized masks 300 (corresponding to optimized binary masks 206 of FIG. 2), and benchmark masks 302, 304, and 306 (respectively for the Variable Density, Uniform Random, and Cartesian sub-sampling patterns), each for two levels of sub-sampling rates: R=10 and R=20. The sub-sampling patterns in FIG. 3 are in 2D k-space, and black dots indicate the points at which a sample is acquired. Representative instantiations are visualized in FIG. 3 for the random masks, and calibration regions 301 are indicated for the conventional sub-sampling patterns.

The Uniform Random and Variable Density patterns were randomly generated by drawing independent Bernoulli samples. For Uniform Random patterns, the probability value at each k-space point was the same and equal to the desired sparsity level. For Variable Density patterns, the probability value at each k-space point was chosen from a Gaussian distribution, centered at the k-space origin. The proportionality constant was set to achieve the desired sparsity level. The Cartesian sub-sampling pattern is deterministic, and yields a k-space trajectory that is straightforward to implement. FIG. 3 visualizes these masks. In FIG. 3, the R=10 and R=20 sub-sampling rates correspond to two sparsity levels: 10% and 5%.

Table 1 below lists run time statistics for the different reconstruction methods, computed on the test subjects. For the U-Net, run-times for both a graphics processing unit (GPU) (NVidia Titan Xp) and central processing unit (CPU) are provided. As shown in Table 1, the U-Net model is significantly faster than the other reconstruction methods, which are all iterative. This speed, combined with the fact that the neural network model is differentiable, enabled use of the U-Net in the end-to-end learning of LOUPE, and optimization the sub-sampling pattern.

TABLE 1

Average per volume run times (in sec) for different reconstruction methods. All except U-Net (GPU) were evaluated on a CPU-a dual Intel Xeon (E5-2640, 2.4 GHz).

| ALOHA | TGV | BM3D | U-Net] (CPU) | U-Net (GPU) |
|---|---|---|---|---|
| 498 ± 43.9 | 492 ± 33.8 | 1691.1 ± 216.4 | 55.9 ± 0.3 | 1.6 ± 0.4 |

Referring again to FIG. 3, under-sampling patterns 300 show the optimized sub-sampling mask that was computed by the LOUPE operations described herein on T1-weighted brain MRI scans from one hundred training subjects. As can be seen in FIG. 3, the resulting masks 300 have similarities with to the Variable Density masks. While it does not include a calibration region, it exhibits a denser sampling pattern closer to the origin of k-space. However, at high frequency values, the relative density of the optimized masks 300 is much smaller than the density of the Variable Density mask.

Figure 4:
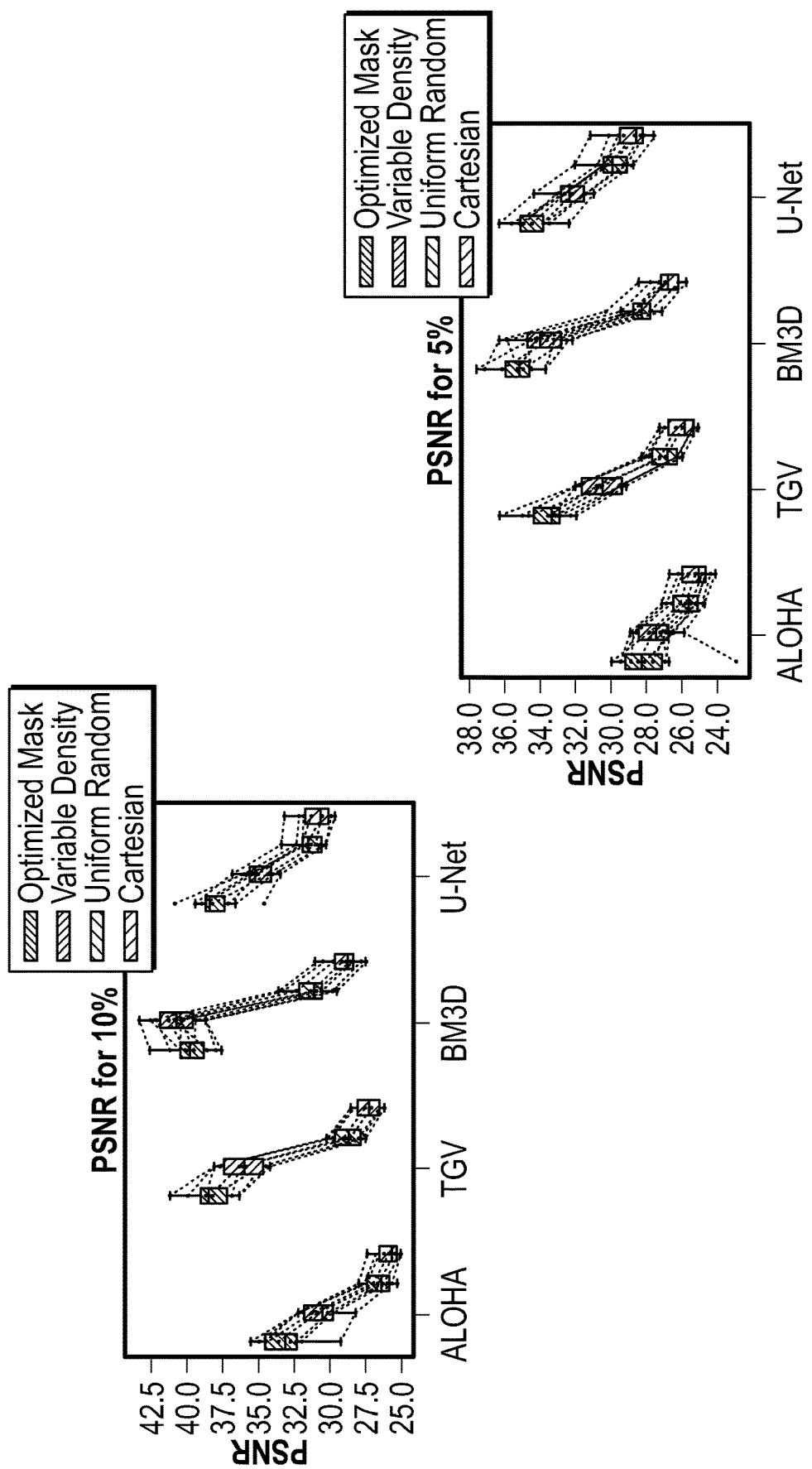
FIG. 4 illustrates statistical results from an empirical analysis of various sub-sampling masks and reconstruction models, according to aspects of the disclosure.

FIG. 4 includes box plots for subject-level PSNR values of reconstructions obtained with four reconstruction methods, four different masks, in separate plots for the two sub-sampling rates. In FIG. 4, for each plot, the results are shown by four sets of boxes, each set corresponding to a reconstruction model, and each box within each set corresponding to a sub-sampling mask, as indicated in the figure. For each box in the figure, one or more dots indicate the PSNR value for a single test subject across slices. For each box, a horizontal line therewithin shows the median value, and the vertical error bars indicate the most extreme (non-outlier) data points.

As can be seen in FIG. 4, the Cartesian and Uniform masks overall yielded worse reconstructions than the Variable Density and Optimized masks. In all except a single scenario, the Optimized mask significantly outperformed other masks (false detection rate (FDR) corrected q<0.01 on paired t-tests). The only case where the Optimized mask was not the best performer was for the 10% sub-sampling rate, coupled with the BM3D reconstruction method. With the 10% sub-sampling rate, coupled with the BM3D reconstruction method, the PSNR values were slightly worse than the best-performing conventional mask, that of Variable Density.

Figure 5:
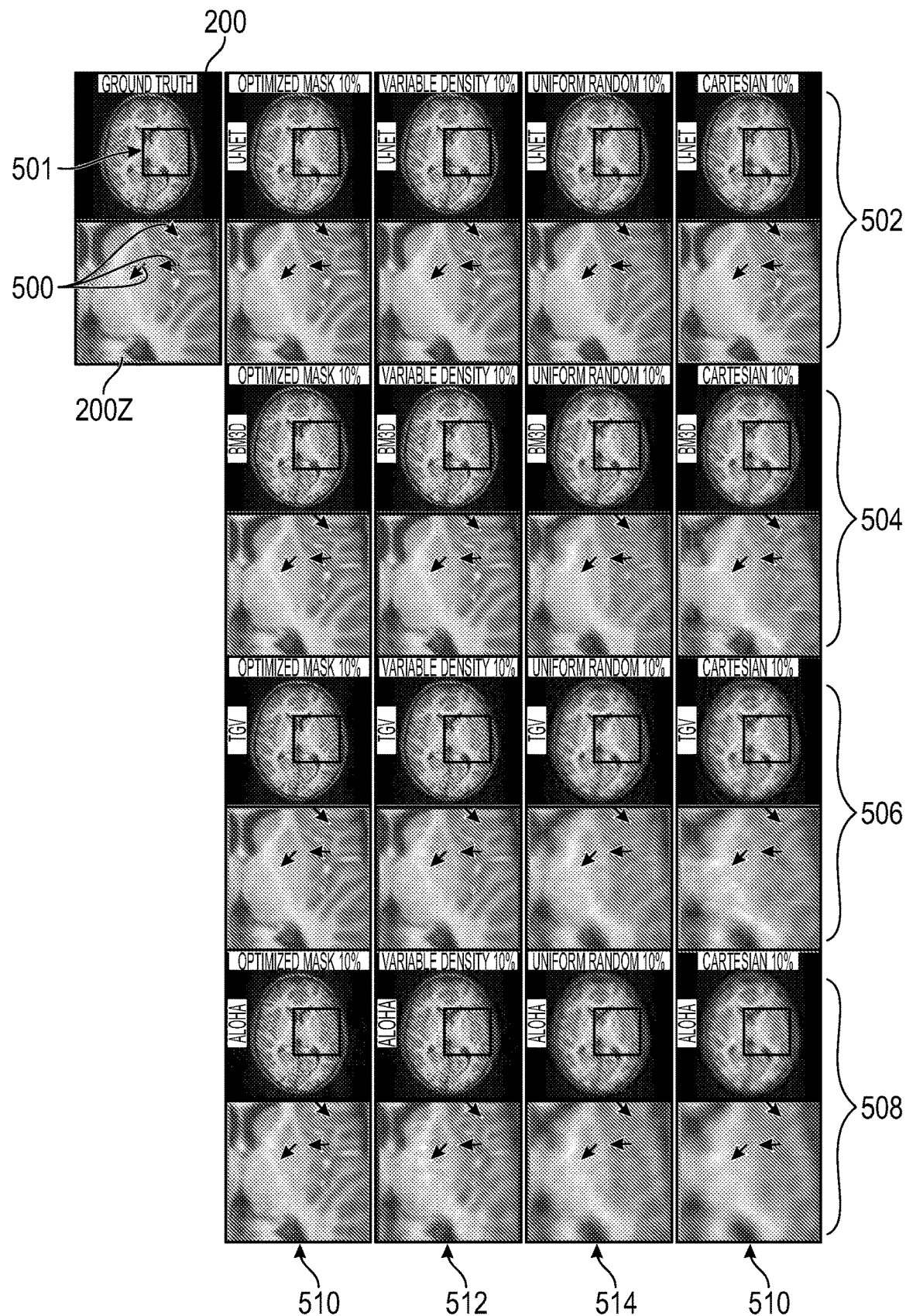
FIG. 5 illustrates reconstructed images corresponding to a ground truth image from an empirical analysis of various sub-sampling masks and reconstruction models, according to aspects of the disclosure.
Figure 6:
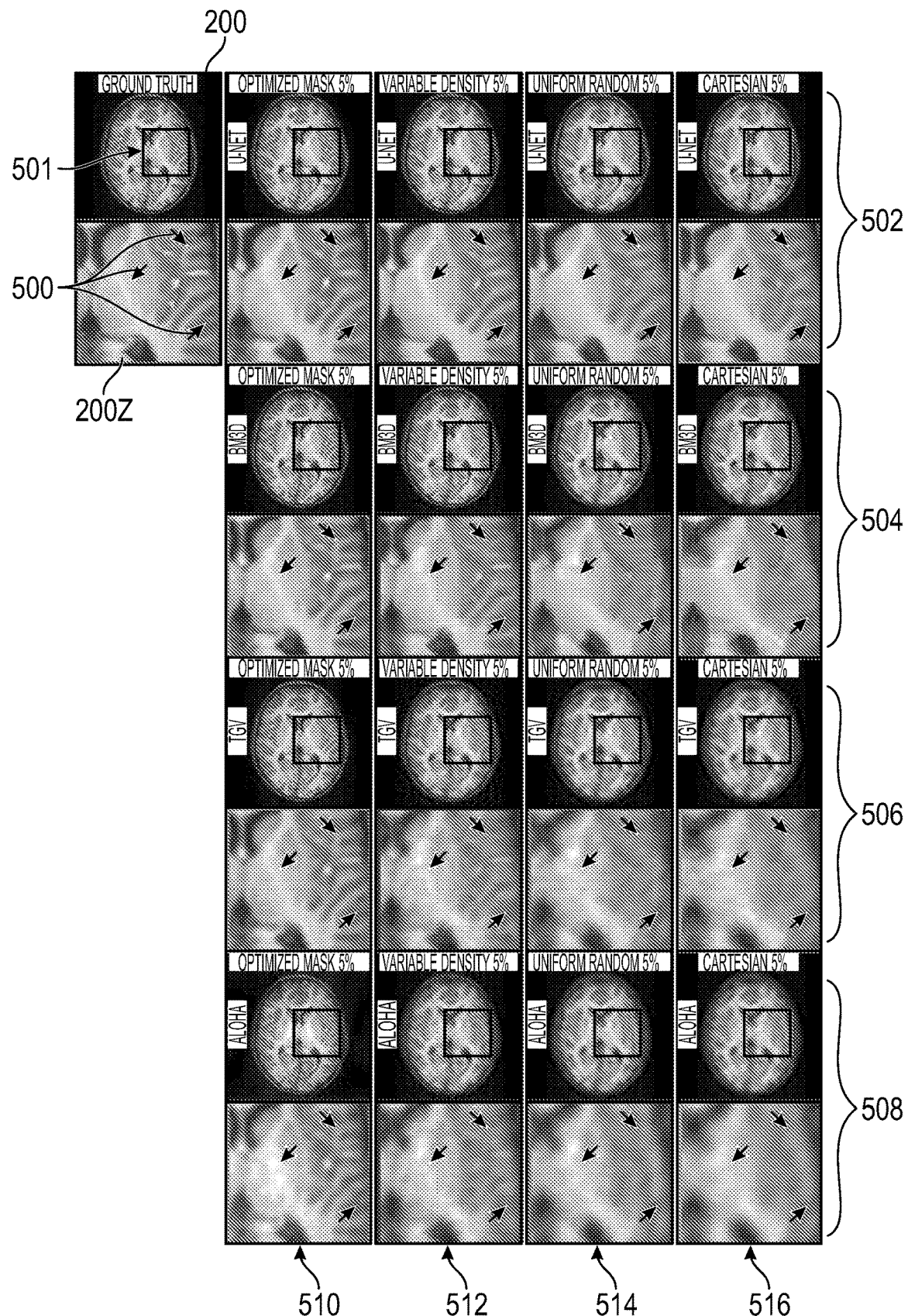
FIG. 6 illustrates reconstructed images corresponding to a ground truth image from an empirical analysis of various sub-sampling masks and reconstruction models using a different sampling rate than used to generate the images of FIG. 5, according to aspects of the disclosure.

While the quantitative results in FIG. 4 give a sense of overall quality, it can also be very informative to visually inspect the reconstructions. FIGS. 5 and 6 show typical examples, respectively for R=10 and R=5, of reconstructed images generated with the various reconstruction models and sub-sampling masks.

In particular, FIGS. 5 and 6 each show an input (ground truth) image 200 and a zoomed image 200Z of a portion 501 of that input image. Also shown in each of FIGS. 5 and 6 are reconstructed images, and zoomed portions thereof, for each reconstruction model/sub-sampling mask pair described above in connection with the empirical analysis. In FIGS. 5 and 6, reconstructed images generated using the optimized (LOUPE) under-sampling masks 114 are shown in column 510, and reconstructed images respectively generated using the Variable Density, Uniform Random, and Cartesian sub-sampling masks are shown in columns 512, 514, and 516. In FIGS. 5 and 6, reconstructed images generated using the optimized (LOUPE) U-Net model 116 with the optimized under-sampling mask, and using a standard U-Net model with the conventional masks are shown in row pair 502, and reconstructed images respectively generated using the BM3D, TGV, and ALOHA reconstruction models are shown in row pairs 504, 506, and 508.

FIGS. 5 and 6 illustrate that the optimized masks 114 yielded reconstructions with higher image quality that capture much more anatomical detail (e.g., highlighted with arrows 500 in the pictures) than what conventional masks yielded. In particular, in this example, the higher quantitative image quality corresponds to a higher visual image quality in which the cortical folding pattern and the boundary of the putamen—a sub-cortical structure—were much more discernible in the images generated using the optimized mask 114. The difference in reconstruction quality between the different methods can also be appreciated. Overall, U-Net and BM3D models offer more faithful (e.g., higher image quality) reconstructions that can be recognized visually in the zoomed-in views.

Figures 7, 8:
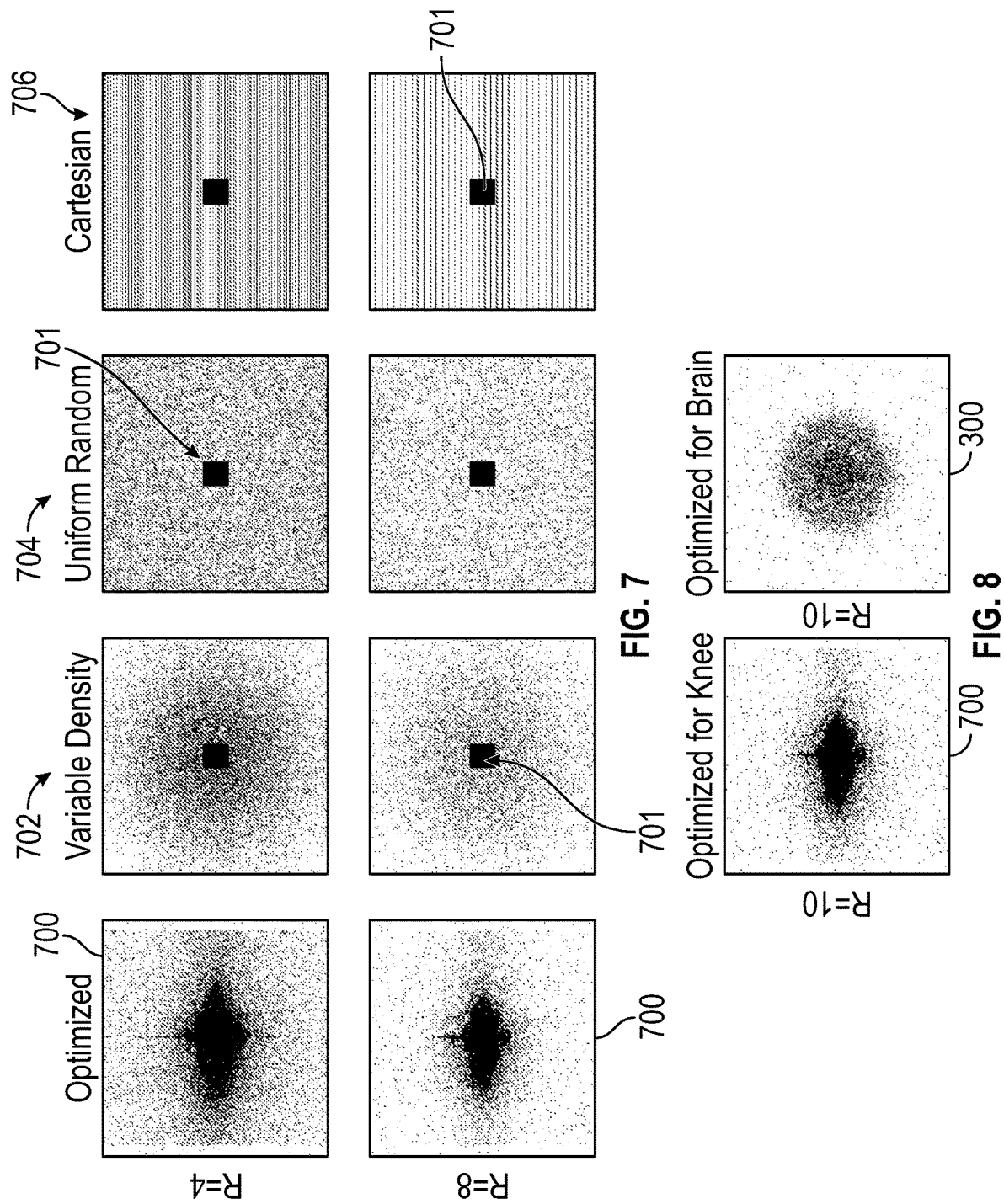
FIG. 7 illustrates various sub-sampling masks for a knee scan, according to aspects of the disclosure.
FIG. 8 shows a comparison of the optimized sub-sampling mask of FIG. 3 for a brain scan with the optimized sub-sampling mask of FIG. 7 for a knee scan, according to aspects of the disclosure.

In the empirical analysis, reconstructions were also performed for a set of knee MRI scans. FIGS. 7 and 9-11 show the results of the empirical analysis of the knee scans, and FIG. 8 shows a comparison of the optimized under-sampling masks 114 for the brain and knee scans. In the reconstructions of the knee MRI scans, the BM3D, TGV, and U-Net reconstruction models, and a Low-Rank Modeling of Local k-Space Neighborhoods (LORAKS) model were used.

Knee scan reconstruction experiments were conducted using the New York University (NYU) fastMRI dataset, which is an openly available, large-scale, public data set of raw k-space data of knee scans. The data set originally includes 2D coronal knee scans acquired with two pulse sequences that result with Proton Density (PD) and Proton Density Fat Su-pressed (PDFS) weighted images. The multi-coil knee scans were collected from four different MRI scanners: Skyra (3T), Prisma (3T), Biograph mMR (3T) and Aera (1.5T). The reconstructions described herein used the provided emulated single-coil (ESC) k-space data of scans, which is derived from raw 15-channel multi-coil data and linearly combined to fit the ground truth of root mean squares solution in a least-squares sense. Amongst the four scanners, the Biograph mMR (3T) scans were used for the reconstruction experiments, due to the appropriate number and quality of the scans. One hundred volumes of scan data were used for training from the official provided training file, and the provided validation file was split into ten volumes for validation and ten volumes for test, due to original test file not having the fully sampled ground truth scans for challenge purposes. The provided sequence parameters were: Echo train length of 4, matrix size of 320×320, in-plane resolution of 0.5 mm×0.5 mm, slice thickness of 3 mm and no gap between slices. The time of repetition (TR) varied between 2200 and 3000 ms and the Echo Time (TE) ranged between 27 and 34 ms. Training volumes had 38±4 slices, where the validation volumes had 37±3 and test volumes had 38±4.

Each set (training, validation, and test) had differing slice sizes amongst volumes. After taking the Inverse Fourier Transform (IFFT) of the ESC k-space data, and rotating and flipping the images to match the orientation in the fastMRI documentation, the central 320×320 pixels were cropped as suggested and normalized the magnitude within each volume.

The U-Net configuration was also used for the reconstruction experiments with the NYU fastMRI scans, and only differed in terms of image size and two channel input layer that accepts complex valued images. In the described experiments, the model was trained with the Adam optimizer, with an initial learning rate of 0.001 and a batch size of 12. A constraint of a 32×32 central calibration region was imposed on the mask. Furthermore, a linearly increasing slope after each epoch was used for the sigmoid in Eq. (4) for a facilitated optimization and better approximation of the binary mask.

FIG. 7 shows optimized and benchmark masks for two levels of sub-sampling rates for the NYU fastMRI knee scan data set: R=4 and R=8. In particular, FIG. 7 shows examples of optimized masks 700 (corresponding to optimized binary masks 206 of FIG. 2) for the knee scans, and benchmark masks 702, 704, and 706 (respectively for the Variable Density, Uniform Random, and Cartesian sub-sampling patterns), each for the two levels of sub-sampling rates: R=4 and R=8. The sub-sampling patterns in FIG. 7 are in 2D k-space, and black dots indicate the points at which a sample is acquired. Representative instantiations are visualized in FIG. 7 for the random masks, and calibration regions 701 are indicated for the conventional sub-sampling patterns.

As with the brain scans associated with FIG. 3, the Uniform Random and Variable Density patterns of FIG. 7 were randomly generated by drawing independent Bernoulli samples. For Uniform Random patterns, the probability value at each k-space point was the same and equal to the desired sparsity level. For Variable Density patterns, the probability value at each k-space point was chosen from a Gaussian distribution, centered at the k-space origin. The proportionality constant was set to achieve the desired sparsity level. The Cartesian sub-sampling pattern is deterministic, and yields a k-space trajectory that is straightforward to implement. FIG. 7 visualizes these masks for the knee scans. In FIG. 7, the R=4 and R=8 sub-sampling rates correspond to two sparsity levels: 25% and 12.5%.

Under-sampling patterns 700 show that the optimized (under-sampled) mask 114 has a non-symmetrical structure, compared to the optimized mask for the brain data set (see FIG. 3) and to the conventional sub-sampling masks. Although the optimized mask 700 is comparable to Variable Density mask in terms of emphasizing the lower frequencies, it is apparent that the horizontal frequencies are favored significantly more than the vertical frequencies in the optimized masks 700. This apparent symmetry difference between the optimized masks for two distinct data sets shows the sensitivity of the systems and methods disclosed herein to anatomical differences, and confirms that the disclosed optimal masks are data driven masks.

FIG. 8 shows a side-by-side comparison of the two optimized masks 300 and 700 for the brain and knee anatomy, respectively. The masks 300 and 700 share the behavior of sudden drop of density from lower to higher frequencies, however differ significantly as the knee mask favors the horizontal frequencies more due to the knee anatomy and tissue being more continuous in vertical alignment and having the majority of the contrast change in the horizontal alignment.

Figure 9:
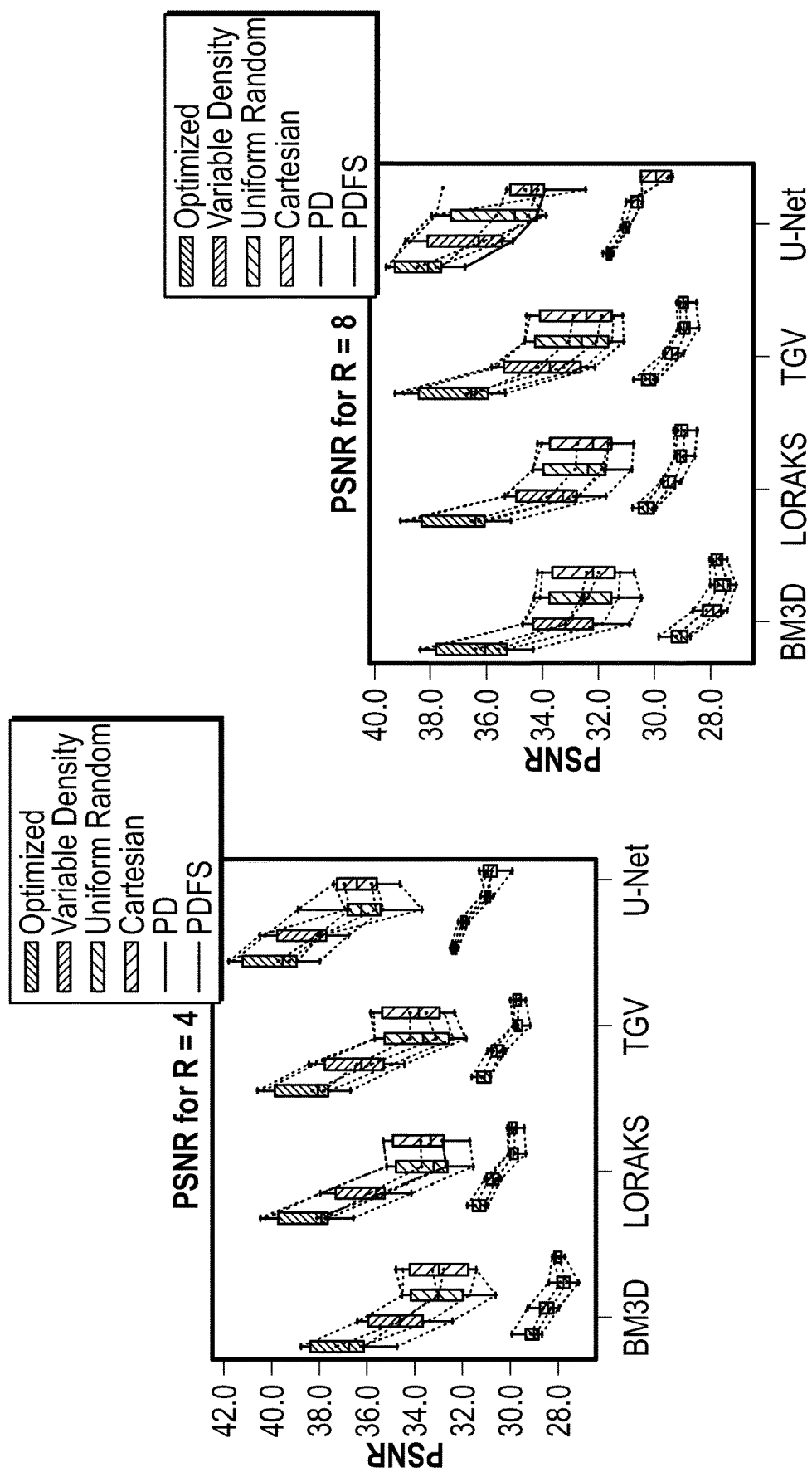
FIG. 9 illustrates statistical results from an empirical analysis of various sub-sampling masks and reconstruction models for a knee scan, according to aspects of the disclosure.

FIG. 9 includes box plots for subject-level PSNR values of reconstructions obtained with four reconstruction methods, four different masks, for each of the PD and PDFS datasets, in two plots corresponding to the two sub-sampling rates for the NYU fastMRI scans. The data presented in FIG. 9 is structured similarly to FIG. 4, and shows that the U-Net configuration with the optimized mask yields the best PSNR values, in both sub-sampling rates compared to other mask configurations and reconstruction methods, for each subject. Variable density has the second best reconstruction quality after the optimized mask, similar to the results for the ABIDE (brain scan) data set. The PSNR results within each reconstruction method and mask configuration show a division between the data set. The test data set includes data for six subjects with PD weighted images and four subjects with PDFS weighted images. The fat suppression operation inherently lowers the signal level, as fat has the highest levels of signal in an MRI scans, and yields a noisy image, where small details are more apparent, whereas the PD weighted scans that still have the fat tissue have inherently higher SNR. Therefore, as shown in FIG. 9, the PD scans yield higher PSNR values in reconstruction compared to the PDFS scans. Overall, the optimized mask yields the highest PSNR in each reconstruction method compared to other mask configurations both for PD and PDFS scans, while the difference in PSNR for PD scans are more apparent.

Figure 10:
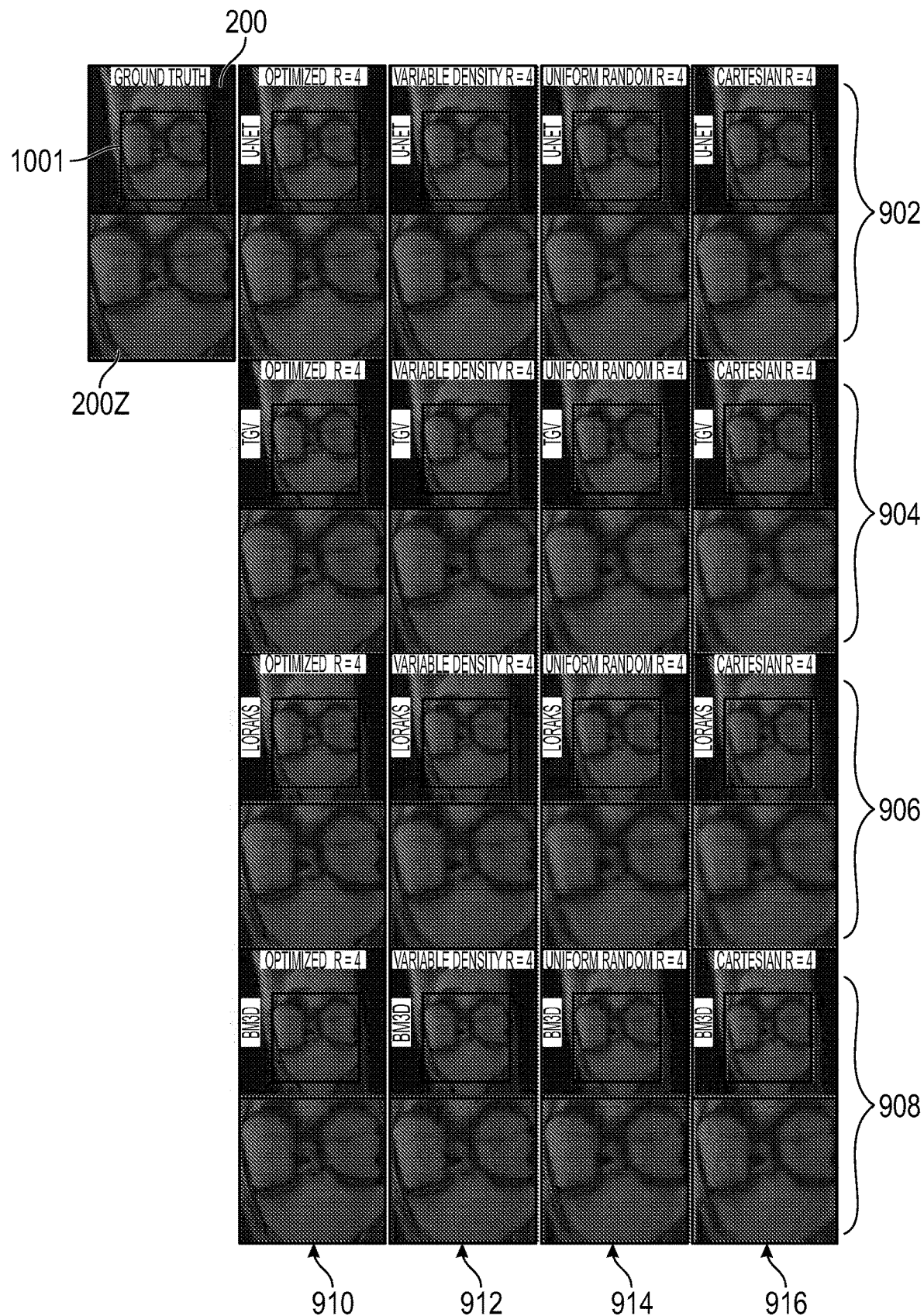
FIG. 10 illustrates reconstructed images corresponding to a ground truth image from a knee scan from an empirical analysis of various sub-sampling masks and reconstruction models, according to aspects of the disclosure.
Figure 11:
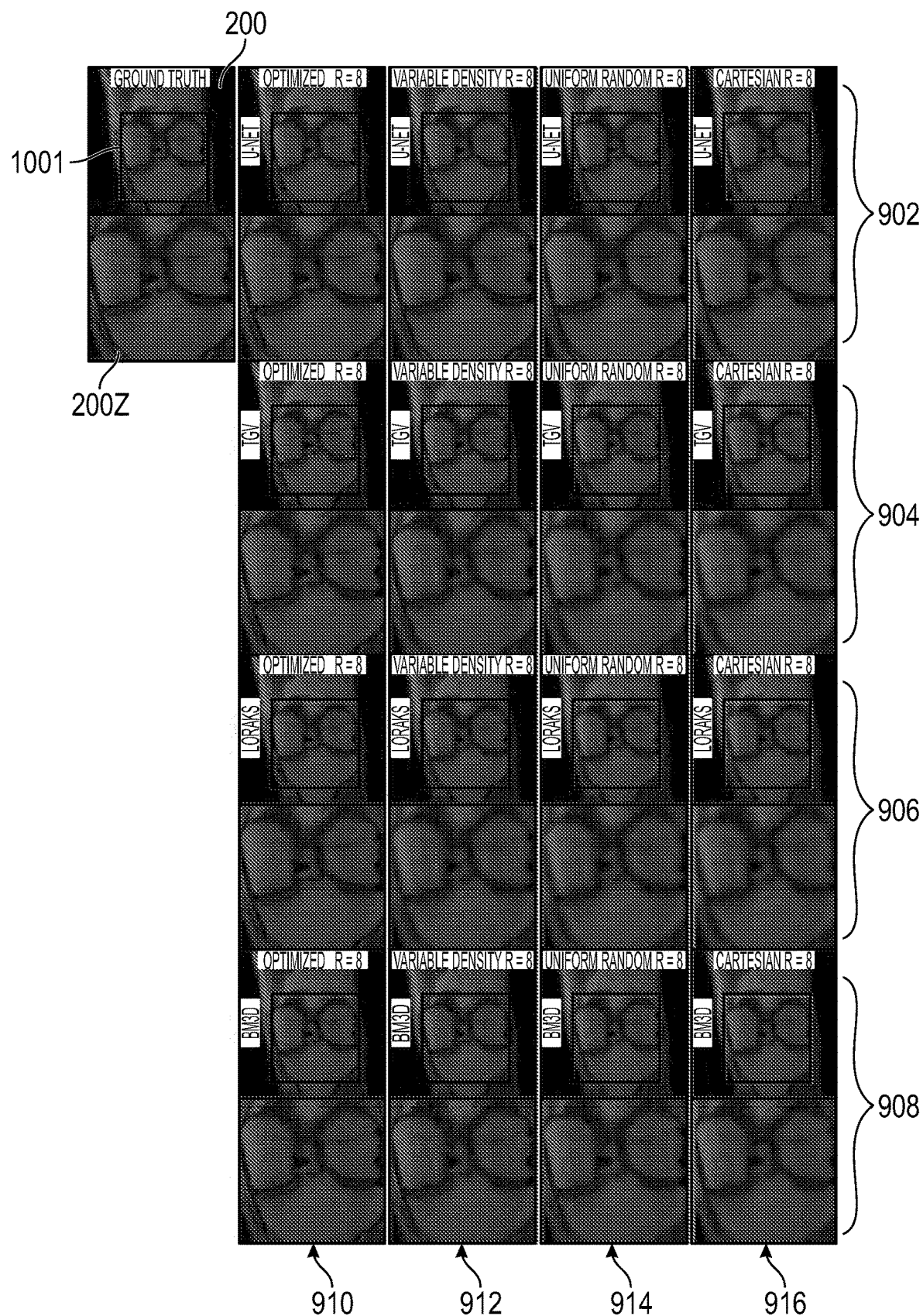
FIG. 11 illustrates reconstructed images corresponding to the ground truth image of the knee scan, from an empirical analysis of various sub-sampling masks and reconstruction models using a different sampling rate than used to generate the images of FIG. 10, according to aspects of the disclosure.

While the quantitative results in FIG. 9 give a sense of overall quality of the various knee scan reconstructions, it can also be very informative to visually inspect the reconstructions. FIGS. 10 and 11 show typical examples, respectively for R=4 and R=8, of reconstructed images generated with the various reconstruction models and sub-sampling masks for the NYU fastMRI knee scan data.

In particular, FIGS. 10 and 11 each show an input (ground truth) image 200 from the NYU fastMRI knee scans, and a zoomed image 200Z of a portion 1001 of that input image. Also shown in each of FIGS. 10 and 11 are reconstructed images of the knee scans and zoomed portions thereof, for each reconstruction model/sub-sampling mask pair described above in connection with the empirical analysis. In FIGS. 10 and 11, reconstructed images generated using the optimized (LOUPE) under-sampling masks 114 are shown in column 910, and reconstructed images respectively generated using the Variable Density, Uniform Random, and Cartesian sub-sampling masks are shown in columns 912, 914, and 916. In FIGS. 10 and 11, reconstructed images generated using the optimized (LOUPE) U-Net model 116 with the optimized under-sampling mask, and using a standard U-Net model with the conventional masks are shown in row pair 902, and reconstructed images respectively generated using the TGV, LORAKS, and BM3D reconstruction modes are shown in row pairs 904, 906, and 908.

As with the brain scan images in FIGS. 5 and 6, the superiority of the LOUPE reconstruction quality and faithfulness to the details is also apparent in the visual inspections of the reconstructed images from the NYU fastMRI dataset, as shown in FIGS. 10 and 11. FIGS. 10 and 11 depict a representative PD weighted image of a subject from the test data set. The optimized mask shows robustness against blurring effects and phantom artifacts compared to benchmark mask configurations in each of the reconstruction method. As can be seen in FIGS. 10 and 111, the U-Net reconstruction with the optimized mask yields the best reconstruction results overall and appears less prone to artifacts, even for other benchmark mask configurations.

Figure 12:
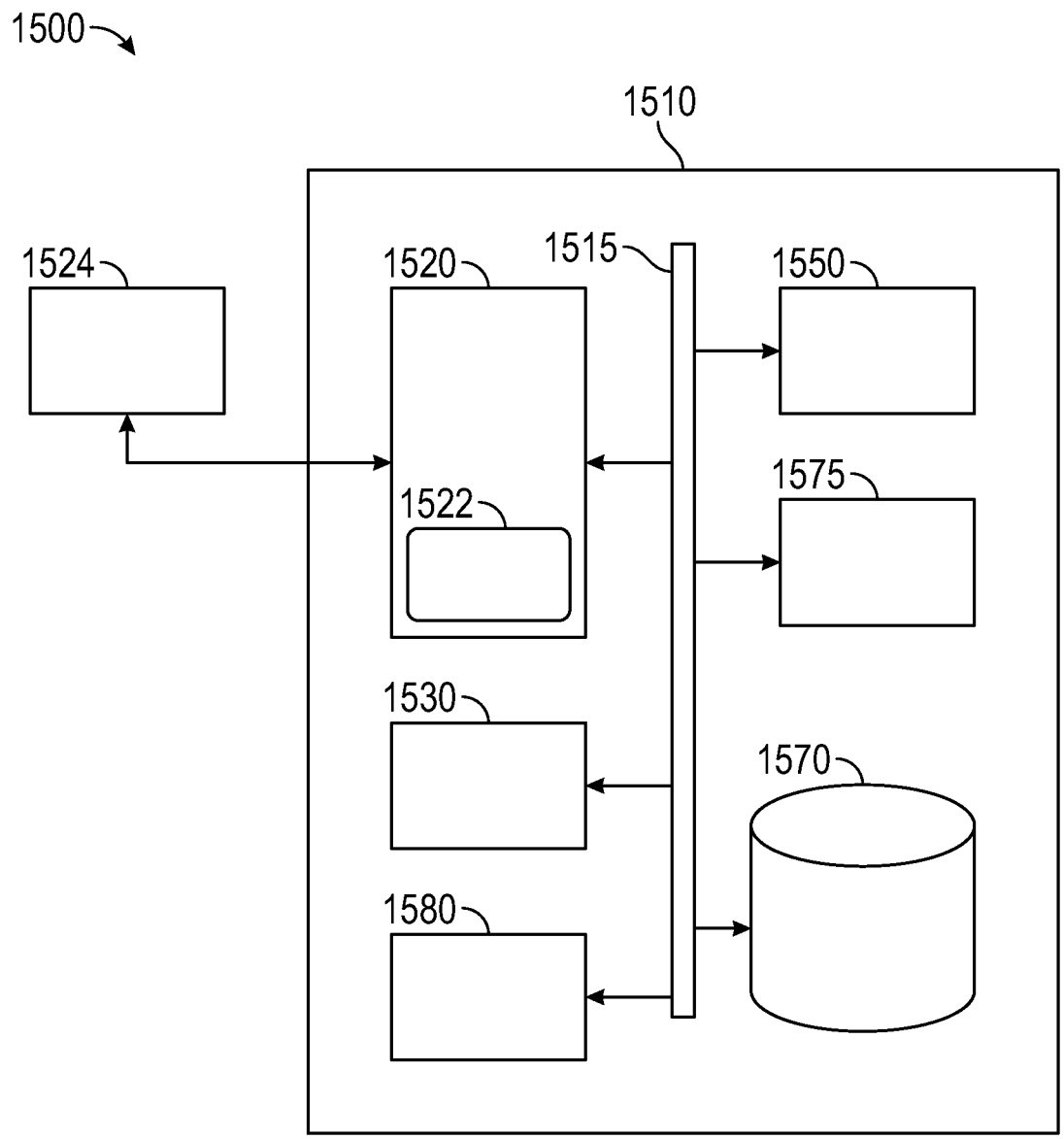
FIG. 12 schematically illustrates a block diagram of an example computing system, according to aspects of the disclosure.

FIG. 12 illustrates a block diagram of an example computing system 1500. In some implementations, the computing system 1500 may be utilized in implementing the training system 102, reconstruction system 104, and/or imaging system 106, and/or any of the processors or modules within the training system 102, reconstruction system 104, and/or imaging system 106 illustrated in FIG. 1.

In broad overview, a computing device 1510 of computing system 1500 includes at least one processor 1550 for performing actions in accordance with instructions and one or more memory devices 1530 or 1575 for storing instructions and data. The illustrated example computing system 1510 includes one or more processors 1550 in communication, via a bus 1515, with at least one network interface controller 1520 with network interface ports 1522 connecting to other computing devices 1524, memory 1570, and any other devices 1580, e.g., an I/O interface. Generally, a processor 1550 will execute instructions received from memory. The processor 1550 illustrated incorporates, or is directly connected to, cache memory 1575.

In more detail, the processor 1550 may be any logic circuitry that processes instructions, e.g., instructions fetched from the memory 1570 or cache 1575. In many embodiments, the processor 1550 is a microprocessor system or special purpose processor. The computing device 1500 may be based on any processor, or set of processors, capable of operating as described herein. In some implementations, the processor 1550 can be capable of implementing and/or executing any of the LOUPE systems and methods described herein, such as in connection with FIGS. 1 and 2. The processor 1550 may be a single core or multi-core processor. The processor 1550 may be multiple processors. In some implementations, the processor 1550 can be configured to run multi-threaded operations. In some implementations, the processor 1550 may host one or more virtual machines or containers, along with a hypervisor or container manager for managing the operation of the virtual machines or containers.

The memory 1570 may be any device suitable for storing computer readable data. The memory 1570 may be a device with fixed storage or a device for reading removable storage media. Examples include all forms of non-volatile memory, media and memory devices, semiconductor memory devices (e.g., EPROM, EEPROM, SDRAM, and flash memory devices), magnetic disks, magneto optical disks, and optical discs (e.g., CD ROM, DVD-ROM, and BluRay® discs). A computing system 1500 may have any number of memory devices 1570. In some implementations, the memory 1570 can include instructions corresponding to forward model 108, machine-learning model 109, or reconstruction models 116 (as examples) described with reference to FIG. 1. In some implementations, the memory 1570 supports virtualized or containerized memory accessible by virtual machine or container execution environments provided by the computing device 1510.

The cache memory 1575 is generally a form of computer memory placed in close proximity to the processor 1550 for fast read times. In some implementations, the cache memory 1575 is part of, or on the same chip as, the processor 1550. In some implementations, there are multiple levels of cache 1575, e.g., L2 and L3 cache layers.

The network interface controller 1520 manages data exchanges via the network interfaces 1522 (also referred to as network interface ports). The network interface controller 1520 handles the physical and data link layers of the OSI model for network communication. In some implementations, some of the network interface controller's tasks are handled by the processor 1550. In some implementations, the network interface controller 1520 is part of the processor 1550. In some implementations, a computing device 1510 has multiple network interface controllers 1520. The network interfaces 1522 are connection points for physical network links. In some implementations, the network interface controller 1520 supports wireless network connections and an interface port 1522 is a wireless receiver/transmitter. Generally, a computing device 1510 exchanges data with other computing devices via physical or wireless links to a network interfaces. In some implementations, the network interface controller 1520 implements a network protocol such as Ethernet.

The other computing devices 1524 are connected to the computing device 1510 via a network interface port 1522. The other computing devices may be peer computing devices, network devices, or any other computing device with network functionality. For example, a first computing device 1524 may be a network device such as a hub, a bridge, a switch, or a router, connecting the computing device 1510 to a data network such as the Internet.

The other devices 1580 may include an I/O interface, external serial device ports, and any additional co-processors. For example, a computing system 1510 may include an interface (e.g., a universal serial bus (USB) interface) for connecting input devices (e.g., a keyboard, microphone, mouse, or other pointing device), output devices (e.g., video display, speaker, or printer), or additional memory devices (e.g., portable flash drive or external media drive). In some implementations, a computing device 1500 includes an additional device 1580 such as a coprocessor, e.g., a math co-processor can assist the processor 1550 with high precision or complex calculations.

The systems and methods described herein provide a novel learning-based approach to simultaneously optimize the sub-sampling pattern and reconstruction model. The experiments described herein, on retrospectively under-sampled brain MRI scans, show that the disclose optimized under-sampling mask and associated reconstruction models can yield reconstructions that are of higher quality than those computed from other widely-used under-sampling masks.

It should also be appreciated that various modifications and/or additions to the systems and methods described herein are contemplated. As a first example, sampling associated cost is captured with an L1 penalty in some of the examples described herein. However, it should be appreciated that alternate metrics can be used that may better capture the true cost of a k-space trajectory, which is constrained by hardware limitations. As a second example, in the LOUPE examples described herein in connection with the experimental analysis, the L1 norm is used for reconstruction loss. However, it should be appreciated that this can also be replaced with alternate metrics, such as those based on adversarial learning or emphasizing subtle yet important anatomical details and/or pathology. As a third example, some or all of the LOUPE operations described herein can be combined with a multi-coil parallel imaging approach to obtain even higher levels of acceleration. As a fourth example, optimization of sub-sampling patterns are described in detail herein for brain and knee MRI scans. However, it should be appreciated that optimized sub-sampling patterns for other MRI sequences and/or other organ domains can also be generated using the systems and methods described herein, including for other compressed sensing and communication applications. Overall, the disclosed systems and methods can be used in other compressed sensing applications beyond medical imaging and further extend to communication and other signal processing related applications.

It has been discovered that, even with an aggressive 8-fold acceleration rate, the LOUPE reconstructions generated by the systems and methods disclosed herein contain much of the anatomical detail that was missed by alternative masks and reconstruction methods.

Implementations of the portions of the subject matter and the operations described in this specification can be implemented in digital electronic circuitry, or in computer software embodied on a tangible medium, firmware, or hardware, including the structures disclosed in this specification and their structural equivalents, or in combinations of one or more of them. Implementations of the subject matter described in this specification can be implemented as one or more computer programs embodied on a tangible medium, i.e., one or more modules of computer program instructions, encoded on one or more computer storage media for execution by, or to control the operation of, a data processing apparatus. A computer storage medium can be, or be included in, a computer-readable storage device, a computer-readable storage substrate, a random or serial access memory array or device, or a combination of one or more of them. The computer storage medium can also be, or be included in, one or more separate components or media (e.g., multiple CDs, disks, or other storage devices). The computer storage medium may be tangible and non-transitory.

The operations described in this specification can be implemented as operations performed by a data processing apparatus on data stored on one or more computer-readable storage devices or received from other sources. The operations may be executed within the native environment of the data processing apparatus or within one or more virtual machines or containers hosted by the data processing apparatus.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other system suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers or one or more virtual machines or containers that are located at one site or distributed across multiple sites and interconnected by a communication network. Examples of communication networks include a local area network ("LAN") and a wide area network ("WAN"), an inter-network (e.g., the Internet), and peer-to-peer networks (e.g., ad hoc peer-to-peer networks).

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

References to "or" may be construed as inclusive so that any terms described using "or" may indicate any of a single, more than one, and all of the described terms. The labels "first," "second," "third," and so forth are not necessarily meant to indicate an ordering and are generally used merely to distinguish between like or similar items or elements.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

What is claimed is:

1. A method of training a MRI image reconstruction system, comprising:
providing a set of input MRI images, wherein the input MRI images are all images of a same organ from different subjects and wherein each image from the set of input MRI images have a corresponding image quality and a corresponding k-space; and
processing the input MRI images using a neural network to collectively identify an under-sampling pattern and a reconstruction model, the under-sampling pattern and reconstruction model being specific to the same organ in the input MRI images;
producing new MRI images with the identified under-sampling pattern and reconstruction model, the new MRI images having an image quality that is substantially similar to the image quality of the input MRI images, from under-sampled MRI data to be captured using the identified under-sampling pattern, wherein the under-sampling pattern is configured to cause a k-space of the under-sampled MRI data to be under-sampled relative to the k-space of the input MRI images.

2. The method of claim 1, wherein the neural network comprises a deep neural network.

3. The method of claim 2, wherein the deep neural network comprises a fully-convolutional neural network.

4. The method of claim 1, wherein processing the input MRI images using the neural network comprises performing a stochastic gradient descent operation.

5. The method of claim 1, wherein processing the input MRI images comprises minimizing a loss function that incorporates both a probability mask associated with a test under-sampling pattern and weights of an anti-aliasing network of a reconstruction model to be applied to image data collected using the test under-sampling pattern associated with the probability mask.

6. The method of claim 5, wherein the probability mask comprises an image of probability values in k-space.

7. The method of claim 1, wherein the reconstruction model comprises an anti-aliasing network.

8. The method of claim 1, further comprising identifying a second under-sampling pattern and a second reconstruction model for use in processing MRI data obtained from imaging an organ other than the organ represented in the input MRI images.

9. The method of claim 1, wherein the input MRI images are all images from a same sequence of images of the same organ from different subjects, and
wherein the identified under-sampling pattern and reconstruction model are specific to the same sequence of the images of the same organ of the input MRI images.

10. The method of claim 9, further comprising identifying a second under-sampling pattern and a second reconstruction model for use in processing MRI data obtained from imaging the same organ using a sequence other than the sequence used for the input MRI images.

11. The method of claim 1, wherein processing the input MRI images using the neural network comprises:
down-sampling the k-space of the input MRI images according to a test under-sampling pattern to form under-sampled MRI images each having an image quality that is lower than the image quality of the input MRI images;
generating, using the neural network implemented as an anti-aliasing network, output reconstructed images from the under-sampled MRI images; and
minimizing an unsupervised loss function that is based on a difference between the input MRI images and the output reconstructed images by adjusting weights of the anti-aliasing network and adjusting the test under-sampling pattern.

12. The method of claim 11, wherein the unsupervised loss function is a continuously differentiable function.

13. A system for MRI imaging, the system comprising:
a reconstruction system, comprising:
a memory storing a plurality of reconstruction models and an indicator, for each reconstruction model, of an under-sampling pattern corresponding to that reconstruction model; and
a processor configured to:
receive under-sampled MRI data from an imaging system, wherein the under-sampled MRI data is under-sampled relative to a maximum sampling rate of the imaging system;
receive, from the imaging system, an identifier of an under-sampling pattern with which the under-sampled MRI data was obtained by the imaging system;
identify, using the identifier and the stored indicators, one of the stored reconstruction models corresponding to the under-sampling pattern with which the under-sampled MRI data was obtained by the imaging system; and
process the under-sampled MRI data using the identified one of the stored reconstruction models to generate at least one MRI image, wherein the at least one MRI image has an improved image quality relative to an image quality of the under-sampled MRI data.

14. The system of claim 13, wherein the under-sampled MRI data has a sampling frequency that is below the Shannon-Nyquist limit.

15. The system of claim 13, further comprising the imaging system, the imaging system comprising a memory storing the under-sampling patterns that correspond to the reconstruction models stored at the reconstruction system.

16. The system of claim 13, wherein the improved image quality of the at least one MRI image is substantially similar to an image quality of training data used to train a neural network to generate the plurality of reconstruction models and the corresponding under-sampling patterns.

17. The system of claim 16, wherein the plurality of reconstruction models and the corresponding under-sampling patterns are provided in model/pattern pairs from a single end-to-end training system based on the neural network.

18. A method of training a MRI image reconstruction system, comprising:
providing a set of input MRI images, wherein the input MRI images are all images from a same sequence of images of a same organ from different subjects and wherein each image from the set of input MRI images have a corresponding image quality and a corresponding k-space; and
processing the input MRI images using a neural network to collectively identify an under-sampling pattern and a reconstruction model, the under-sampling pattern and reconstruction model being specific to the same sequence of the images of the same organ of the input MRI images;
producing new MRI images with the identified under-sampling pattern and reconstruction model, the new MRI images having an image quality that is substantially similar to the image quality of the input MRI images, from under-sampled MRI data to be captured using the identified under-sampling pattern, wherein the under-sampling pattern is configured to cause a k-space of the under-sampled MRI data to be under-sampled relative to the k-space of the input MRI images.

19. The method of claim 18, further comprising identifying a second under-sampling pattern and a second reconstruction model for use in processing MRI data obtained from imaging the same organ using a sequence other than the sequence used for the input MRI images.

20. The method of claim 18, wherein the reconstruction model comprises an anti-aliasing network.

* * * * *